United States Patent
Greene et al.

(10) Patent No.: US 8,318,699 B2
(45) Date of Patent: Nov. 27, 2012

(54) TUMOR NECROSIS FACTOR INHIBITORS

(75) Inventors: Mark I Greene, Penn Valley, PA (US); Ramachandran Murali, Drexel Hill, PA (US); Xin Cheng, Wallingford, PA (US); Raphael Ottenbrite, Midlothian, VA (US); Yingxin Xiao, North Potomac, MD (US)

(73) Assignees: The Trustees Of The University Of Pennsylvania, Philadelphia, PA (US); Cephalon, Inc., Wilmington, DE (US)

( * ) Notice: Subject to any disclaimer, the term of this patent is extended or adjusted under 35 U.S.C. 154(b) by 947 days.

(21) Appl. No.: 11/815,134

(22) PCT Filed: Jan. 31, 2006

(86) PCT No.: PCT/US2006/003574
§ 371 (c)(1),
(2), (4) Date: Dec. 4, 2008

(87) PCT Pub. No.: WO2006/038970
PCT Pub. Date: Aug. 10, 2006

(65) Prior Publication Data
US 2009/0221527 A1  Sep. 3, 2009

Related U.S. Application Data

(60) Provisional application No. 60/648,973, filed on Jan. 31, 2005.

(51) Int. Cl.
| | |
|---|---|
| A61K 31/405 | (2006.01) |
| A61K 31/135 | (2006.01) |
| A61K 31/225 | (2006.01) |
| A61K 31/69 | (2006.01) |
| A61K 31/09 | (2006.01) |
| A61K 31/216 | (2006.01) |
| A61K 31/352 | (2006.01) |
| A61K 31/15 | (2006.01) |
| C07D 311/82 | (2006.01) |
| C07D 311/94 | (2006.01) |
| C07D 209/12 | (2006.01) |
| C07F 5/02 | (2006.01) |
| C07C 59/31 | (2006.01) |
| C07C 69/353 | (2006.01) |
| C07C 241/00 | (2006.01) |
| C07C 215/20 | (2006.01) |
| C07C 69/76 | (2006.01) |
| C07C 41/01 | (2006.01) |

(52) U.S. Cl. .......... 514/64; 514/418; 514/454; 514/533; 514/548; 514/639; 514/648; 514/721; 548/487; 549/383; 549/388; 560/140; 560/57; 560/76; 560/85; 562/468; 564/251; 564/327; 568/6; 568/640

(58) Field of Classification Search .................. None
See application file for complete search history.

(56) References Cited

U.S. PATENT DOCUMENTS

| | | | | |
|---|---|---|---|---|
| 1,624,675 | A | * 4/1927 | Preiswerk et al. | ............ 548/487 |
| 6,028,103 | A | 2/2000 | Brugnara et al. | |
| 2004/0002546 | A1 | 1/2004 | Altschuler | |

FOREIGN PATENT DOCUMENTS

| | | |
|---|---|---|
| DE | 19716884 A1 | 10/1997 |
| DE | 10-2004-00260 A1 | 8/2005 |
| EP | 0911633 | 10/1998 |
| JP | 2001-521485 | 11/2001 |
| JP | 2002-519680 | 7/2002 |
| WO | WO 96/08240 | 3/1996 |
| WO | WO 97/34589 | 9/1997 |
| WO | WO 00/01349 | 1/2000 |
| WO | WO 02/05793 A2 | 1/2002 |
| WO | WO 02/05812 A1 | 1/2002 |
| WO | WO 2005/003094 | 2/2005 |
| WO | WO2006083869 | * 8/2006 |

OTHER PUBLICATIONS

MultipleSclerosis, 2008.*
Marketwire, 2008.*
RedOrbit, 2008.*
psoriasis, Weinberg et al., http://findarticles.com/p/articles/mi m0PDG/is 5 4/ai n15396461/ (2011).*
Al-Qawasmeh et al., "Triaryl Methane Derivatives as Antiproliferative Agents", Bioorganic and Medicinal Chemistry Letters, Jan. 19, 2004, 14(2), 347-350.
Cohen-Kashi et al., "Carboxyfluorescein as a Fluorescent Probe for Cytoplasmic Effects of Lymphocyte Stimulation", Spectrochimica Acta, Part A., Molecular and Biomolecular Spectroscopy, Sep. 1997, 53A(10), 1655-1661.
Tamagnone & Sticco, "Synthesis and Laxative Properties of Esters of 1,1,1 -[bis-(p-hydroxyphenyl)-(2-pyridyl)lethane and Related Compounds", Chimie Therapeutique, 1973, 6, 682-685.

* cited by examiner

Primary Examiner — Sun Jae Loewe
(74) Attorney, Agent, or Firm — Woodcock Washburn, LLP

(57) ABSTRACT

The present invention is directed to compounds that are allosteric inhibitors of tumor necrosis factor receptor I, compositions comprising such compounds, and methods of using such compounds and compositions thereof in the treatment of TNF-α mediated conditions.

4 Claims, 4 Drawing Sheets

SEQUENCE LISTING

```
<160> NUMBER OF SEQ ID NOS: 3

<210> SEQ ID NO 1
<211> LENGTH: 172
<212> TYPE: PRT
<213> ORGANISM: Homo sapiens

<400> SEQUENCE: 1

Leu Val Pro His Leu Gly Asp Arg Glu Lys Arg Asp Ser Val Cys Pro
1               5                   10                  15

Gln Gly Lys Tyr Ile His Pro Gln Asn Asn Ser Ile Cys Cys Thr Lys
            20                  25                  30

Cys His Lys Gly Thr Tyr Leu Tyr Asn Asp Cys Pro Gly Pro Gly Gln
        35                  40                  45

Asp Thr Asp Cys Arg Glu Cys Glu Ser Gly Ser Phe Thr Ala Ser Glu
    50                  55                  60

Asn His Leu Arg His Cys Leu Ser Cys Ser Lys Cys Arg Lys Glu Met
65                  70                  75                  80

Gly Gln Val Glu Ile Ser Ser Cys Thr Val Asp Arg Asp Thr Val Cys
                85                  90                  95

Gly Cys Arg Lys Asn Gln Tyr Arg His Tyr Trp Ser Glu Asn Leu Phe
            100                 105                 110

Gln Cys Phe Asn Cys Ser Leu Cys Leu Asn Gly Thr Val His Leu Ser
        115                 120                 125

Cys Gln Glu Lys Gln Asn Thr Val Cys Thr Cys His Ala Gly Phe Phe
    130                 135                 140

Leu Arg Glu Asn Glu Cys Val Ser Cys Ser Asn Cys Lys Lys Ser Leu
145                 150                 155                 160

Glu Cys Thr Lys Leu Cys Leu Pro Gln Ile Glu Asn
                165                 170

<210> SEQ ID NO 2
<211> LENGTH: 32
<212> TYPE: DNA
<213> ORGANISM: artificial
<220> FEATURE:
<223> OTHER INFORMATION: primer

<400> SEQUENCE: 2
aaaaaacata tgtacccctc aggggttatt gg                                32
```

```
<210> SEQ ID NO 3
<211> LENGTH: 50
<212> TYPE: DNA
<213> ORGANISM: artificial
<220> FEATURE:
<223> OTHER INFORMATION: primer
<400> SEQUENCE: 3
ccgctcgagt caatgatgat gatgatgatg tgtggtgcct gagtcctcag          50
```

TUMOR NECROSIS FACTOR INHIBITORS

CROSS REFERENCE TO RELATED APPLICATIONS

The present application is a 371 National Phase of International Application No. PCT/US06/03574, filed Jan. 31, 2006, which claims the benefit under 35 U.S.C. 119(e), of U.S. Provisional Application 60/648,973, filed Jan. 31, 2005, both of which are hereby incorporated herein by reference in their entireties.

FEDERALLY SPONSORED RESEARCH OR DEVELOPMENT

This invention was made in part in the course of research sponsored by the National Institutes of Health grant number RO1-CA89481 and the National Cancer Institute grant number 1PO1 CA89480-04. The U.S. government has certain rights in this invention.

FIELD OF THE INVENTION

The present invention relates to compounds that are allosteric inhibitors of tumor necrosis factor receptor I and methods of use thereof.

BACKGROUND OF THE INVENTION

Research leading to the present invention was supported in part by funds from the National Institutes of Health, the National Cancer Institute, and the Leonard and Madlyn Abramson Family Cancer Research Institute Fund.

Structural changes in proteins can be induced by various physical factors including pH, solvents, ligand binding and oligomerization. Conformational changes can occur at a defined local site or, as observed in multimeric proteins, at a distance from the ligand binding site (allosterism).

Protein function can be altered by conformational changes. Immunoglobulins have been shown to alter the function of proteins by inducing small to large conformational changes, and by affecting the oligomerization of proteins. For example, in the crystal structure of Taq DNA polymerase complex, an antibody inhibited the function of DNA polymerase by inducing a large conformational change in the helix and trapping the protein in a transition state suggesting that altering conformational configuration at distinct sites away from the binding sites might be used to modulate protein function.

It has been generally argued that conformational changes may be a step in substrate/ligand recognition. Several studies from the crystal structures of protein-protein complexes revealed conformational changes ranging from 2-20 Å (0.2-2 nm) either locally or globally between subdomains. In the case of multimeric proteins such as myoglobin or glycogen phosphorylase, with known allosteric sites, defined conformational changes are transmitted through regions of the protein for regulatory or functional effects.

While surface cavities on non-enzymatic classes of proteins have been largely unexplored, inactivation of enzymes has been accomplished by designing competitive or substrate analog inhibitors that bind at active sites. Several therapeutic inhibitors have been developed based on the structure and molecular properties of substrates and these are generally known as "substrate analogs". Small molecule effectors have been identified for enzymes. For example, allosteric inhibitors have been designed and developed based on the knowledge of known and established allosteric binding sites. Small conformational perturbations near the active site/ligand binding sites or polymorphisms near the active site have been suggested to be responsible for resistance to substrate based inhibitors.

Tumor necrosis factor α (TNF-α) is a pleiotropic cytokine produced by activated macrophages/monocytes and lymphocytes. TNF-α is a potent mediator in inflammatory and immune responses, including the recruitment of leukocytes to injured tissues during bacterial and other microbial infections, and following stimulation with inflammatory substances. When present in excessive quantities, TNF-α is known to cause tissue injury, and has been implicated in the pathology associated with inflammatory and autoimmune diseases.

The biological effects of TNF-α, are mediated through two distinct membrane-protein receptors, TNF-RI and TNF-RII (in humans, p55 and p75, respectively), which differ in sequence and molecular mass. TNF-RI is reported to be present at low levels in most, if not all, human cell types, and expression of the TNF-RI gene in humans can be upregulated by infection, interferons, and modulators of second messengers, such as phorbol esters. The extracellular portions of both TNF receptors also exist in soluble forms, which are derived from membrane-bound forms of the receptors by proteolytic cleavage at the cell surface. The soluble TNF receptors retain the ability to bind TNF-α in solution. Soluble TNF receptors have been identified in urine and sera from healthy individuals, and have been shown to be elevated in some chronic diseases and following inoculation with agents that induce TNF-α release.

The pathological effects of TNF-α can be alleviated by administration of soluble TNF-R fragments or anti-TNF-α antibodies. These agents bind circulating TNF-α, thus preventing the binding of TNF-α to TNF-R and lowering TNF-α signaling. TNF-R fragments or anti-TNF-α antibodies have been approved, by the U.S. Food and Drug Administration, for treatment of rheumatoid arthritis, juvenile rheumatoid arthritis, ankylosing spondylitis, psoriatic arthritis, and psoriasis.

The efficacy of TNF-R fragments and anti-TNF-α antibodies in treating TNF-α-mediated conditions demonstrates that reducing signaling through the TNF-α/TNF-R signaling pathway can be used effectively to treat TNF-α-mediated conditions. TNF-R fragments and anti-TNF-α antibodies, however, are expensive to produce. Moreover, these proteinaceous agents require intravenous administration.

There is, therefore, a need in the art for additional agents that reduce signaling through the TNF-α/TNF-R signaling pathway and that can be used for treatment of TNF-α-mediated conditions. Accordingly, the present inventors have discovered small molecule compounds that bind to an allosteric site on TNF-R1, thus inhibiting binding of TNF-α to TNF-R1 and reducing activity of the TNF-α/TNF-R1 signaling pathway. The compounds are useful for treatment of TNF-α mediated conditions.

SUMMARY OF THE INVENTION

The present invention is directed to compounds that are inhibitors of TNF-R1, compositions thereof, and methods of using such compounds and compositions to treat conditions mediated by the TNF-R1/TNF-α signaling pathway.

In certain embodiments, the invention is directed towards compounds represented by formula (I), (II), or (III)

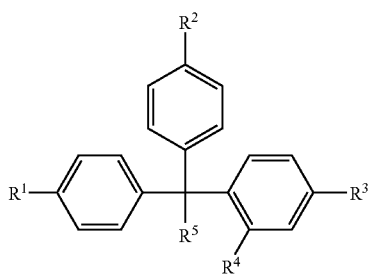
(I)

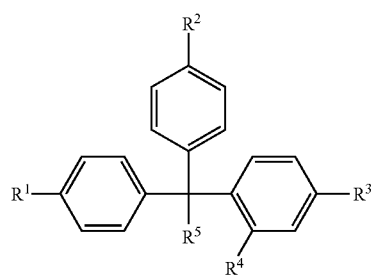
(I)

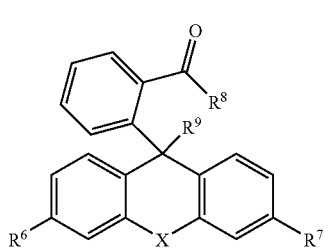
(II)

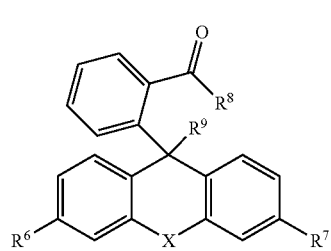
(II)

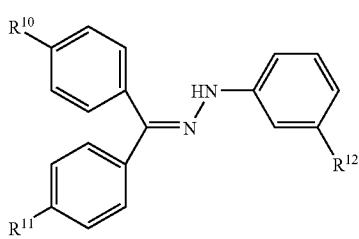
(III)

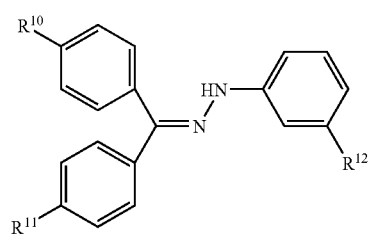
(III)

wherein $R^1$, $R^2$, $R^3$, $R^4$, $R^5$, $R^6$, $R^7$, $R^8$, $R^9$, $R^{10}$, $R^{11}$, and $R^{12}$ are each independently hydrogen, alkyl, hydroxyl, alkoxy, —$NR^{13}R^{14}$, halo, nitro, cyano, borono, aryl, aryloxy, —$(CH_2)_nCOOR^{15}$, —$O(CH_2)_nCOOR^{16}$, —$OC(O)R^{17}$, —$CR^{18}$=NOH, —$CR^{19}R^{20}$NHOH, —$SO_3H$, —$SO_2R^{21}$, —$SO_2NHR^{22}$, —$O(CH_2)_mOR^{23}$, —C(OH)=N(OH), —$C(O)NR^{24}OH$, —$CHR^{25}N(COR^{26})OH$, or —$C(O)R^{27}$ or $R^4$ and $R^5$ together form —$NR^{28}C(O)$—, —$C(O)NR^{29}$—, —C(O)O—, or —$S(O)_2NR^{30}$—, or $R^8$ and $R^9$ together form —O—, —NHC(O)—, —C(O)NH—, —C(O)O—, —$NR^{29}$—, or —$S(O)_2NH$;

$R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{28}$, $R^{29}$, and $R^{30}$ are each independently hydrogen, alkyl, or aryl and $R^{27}$ is alkyl or aryl;

X is absent or is —O—, —$NR^{28}$—, or —S—; and n and m are independently 0, 1, 2, 3, 4, 5, or 6;

with the proviso that if $R^4$ is halogen, $R^5$ is hydrogen, and $R^1$ and $R^2$ are independently hydrogen, methoxy, saturated alkyl, 3-carboxy-4-chlorophenylamino, —$N(CH_2CH_2OH)_2$, or OC(O)Ph, then $R^3$ is not hydrogen, saturated alkyl, methoxy, halogen, carboxy-4-chlorophenylamino, —$N(CH_2CH_2OH)_2$, or OC(O)Ph.

In other embodiments, the invention is directed towards compounds represented by formula (I), (II), or (III):

wherein $R^1$, $R^2$, $R^3$, $R^4$, $R^5$, $R^6$, $R^7$, $R^8$, $R^9$, $R^{10}$, $R^{11}$, and $R^{12}$ are each independently hydrogen, alkyl, hydroxyl, alkoxy, —$NR^{13}R^{14}$, halo, nitro, cyano, borono, aryl, aryloxy, —$(CH_2)_nCOOR^{15}$, —$O(CH_2)_nCOOR^{16}$, —$OC(O)R^{17}$, —$CR^{18}$=NOH, —$CR^{19}R^{20}$NHOH, —$SO_3H$, —$SO_2R^{21}$, —$SO_2NHR^{22}$, —$O(CH_2)_mOR^{23}$, —C(OH)=N(OH), —$C(O)NR^{24}OH$, —$CHR^{25}N(COR^{26})OH$, or —$C(O)R^{27}$ or $R^4$ and $R^5$ together form —$NR^{28}C(O)$—, —$C(O)NR^{29}$—, —C(O)O—, or —$S(O)_2NR^{30}$—, or $R^8$ and $R^9$ together form —O—, —NHC(O)—, —C(O)NH—, —C(O)O—, —$NR^{29}$—, or —$S(O)_2NH$—;

$R^{13}$, $R^{14}$, $R^{15}$, $R^{16}$, $R^{17}$, $R^{18}$, $R^{19}$, $R^{20}$, $R^{21}R^{22}$, $R^{23}$, $R^{24}$, $R^{25}$, $R^{26}$, $R^{28}$, $R^{29}$, and $R^{30}$ are each independently hydrogen, alkyl, or aryl and $R^{27}$ is alkyl or aryl;

X is absent or is —O—, —$NR^{28}$—, or —S—; and n and m are independently 0, 1, 2, 3, 4, 5, or 6;

with the proviso that if $R^4$ is halogen, $R^5$ is hydrogen, and $R^1$ and $R^2$ are independently hydrogen, methoxy, saturated alkyl, 3-carboxy-4-chlorophenylamino, —$N(CH_2CH_2OH)_2$, or OC(O)Ph, then $R^3$ is not hydrogen, saturated alkyl, methoxy, halogen, carboxy-4-chlorophenylamino, —$N(CH_2CH_2OH)_2$, or OC(O)Ph.

In other embodiments, the invention is directed to a compound represented by the formula:

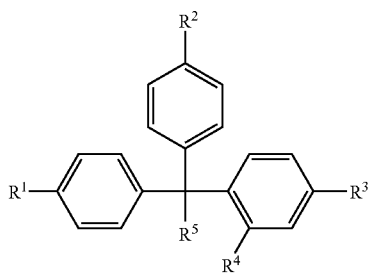
(I)

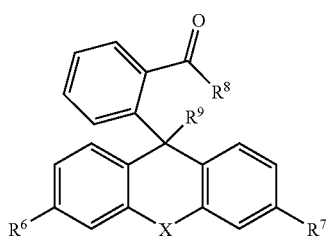
(II)

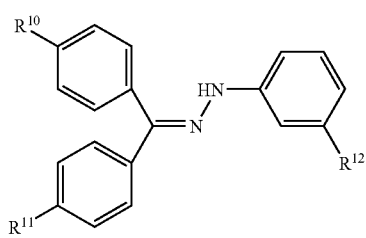
(III)

wherein $R^1$, $R^2$, $R^3$, $R^4$, $R^5$, $R^6$, $R^7$, $R^8$, $R^9$, $R^{10}$, $R^{11}$, and $R^{12}$ are each independently hydrogen, alkyl, hydroxyl, alkoxy, —$NR^{13}R^{14}$, halo, nitro, cyano, borono, aryl, aryloxy, —$(CH_2)_nCOOR^{15}$, —$O(CH_2)_nCOOR^{16}$, —$OC(O)R^{17}$, —$CR^{18}$=NOH, —$CR^{19}R^{20}$NHOH, —$SO_3H$, —$SO_2R^{21}$, —$SO_2NHR^{22}$, —$O(CH_2)_mOR^{13}$, —C(OH)=N(OH), —$C(O)NR^{24}OH$, —$CHR^{25}N(COR^{26})OH$, or —$C(O)R^{27}$ or $R^4$ and $R^5$ together form —$NR^{28}C(O)$—, —$C(O)NR^{29}$—, —C(O)O—, or —$S(O)_2NR^{30}$—, or $R^8$ and $R^9$ together form —O—, —NHC(O)—, —C(O)NH—, —C(O)O—, —$NR^{29}$—, or —$S(O)_2NH$—;

$R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{28}$, $R^{29}$, and $R^{30}$ are each independently hydrogen, alkyl, or aryl and $R^{27}$ is alkyl or aryl;

X is absent or is —O—, —$NR^{28}$—, or —S—; and n and m are independently 0, 1, 2, 3, 4, 5, or 6;

with the proviso that if $R^4$ is halogen, $R^5$ is hydrogen, and $R^1$ and $R^2$ are independently hydrogen, methoxy, saturated alkyl, 3-carboxy-4-chlorophenylamino, —$N(CH_2CH_2OH)_2$, or OC(O)Ph, then $R^3$ is not hydrogen, saturated alkyl, methoxy, halogen, carboxy-4-chlorophenylamino, —$N(CH_2CH_2OH)_2$, or OC(O)Ph;

with the proviso that the compound is not:

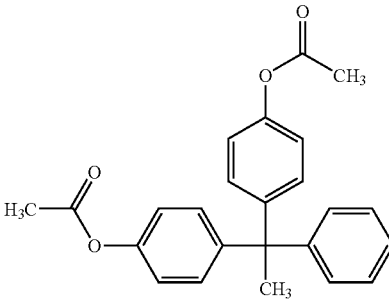

or a salt thereof.

In other embodiments, the invention is directed to a compound represented by the structure:

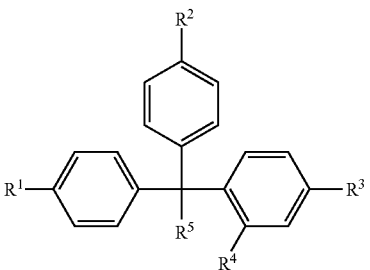

wherein $R^1$ is —$O(CH_2)_nCOOR^9$ or —$OC(O)CH_2R^{31}$;

$R^2$, $R^3$, $R^4$, and $R^5$ are each independently hydrogen, alkyl, hydroxyl, alkoxy, —$NR^{13}R^{14}$, halo, nitro, cyano, borono, aryl, aryloxy, —$(CH_2)_nCOOR^{15}$, —$O(CH_2)_nCOOR^{16}$, —$OC(O)R^{17}$, —$CR^{18}$=NOH, —$CR^{19}R^{20}$NHOH, —$SO_3H$, —$SO_2R^{21}$, —$SO_2NHR^{22}$, —$O(CH_2)_mOR^{23}$, —C(OH)=N(OH), —$C(O)NR^{24}OH$, —$CHR^{25}N(COR^{16})OH$, or —$C(O)R^{27}$ or $R^4$ and $R^5$ together form —$NR^{28}C(O)$—, —$C(O)NR^{29}$—, —C(O)O—, or —$S(O)_2NR^{31}$—;

$R^{13}$, $R^{14}$, $R^{15}$, $R^{16}$, $R^{17}$, $R^{18}$, $R^{19}$, $R^{20}$, $R^{21}R^{22}$, $R^{23}$, $R^{24}$, $R^{25}$, $R^{26}R^{28}$, $R^{29}$, and $R^{30}$ are each independently hydrogen, alkyl, or aryl and $R^{27}$ is alkyl or aryl;

$R^{31}$ is halogen; and n and m are independently 0, 1, 2, 3, 4, 5, or 6;

with the proviso that the compound is not:

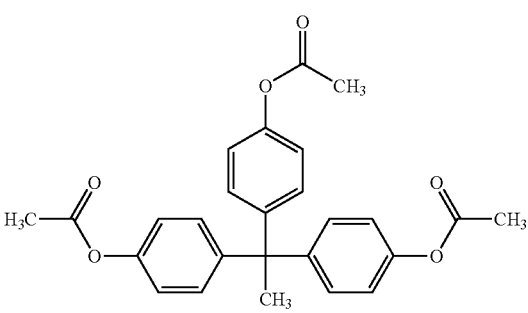

or a salt thereof.

In other embodiments, the invention is directed to a compound represented by the formula:

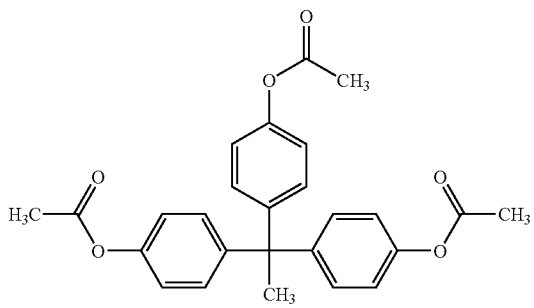

I-9 or a salt thereof.

In other embodiments, the invention is directed to a compound represented by the formula:

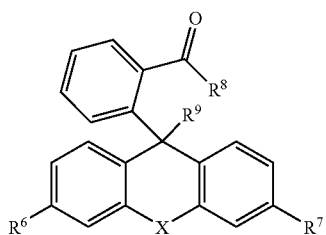

wherein $R^6$, $R^7$, and $R^9$ are each independently hydrogen, $C_{1-6}$ alkyl, $C_{3-7}$ cycloalkyl, hydroxyl, $C_{1-6}$ alkoxy, $-NR^{13}R^{14}$, halogen, nitro, cyano, borono, phenyl, benzyl, benzoyl, phenoxy, benzyloxy, $-(CH_2)_nCOOR^{15}$, $-O(CH_2)_nCOOR^{16}$, $-OC(O)R^{17}$, $-CH=NOH$, $-CH_2NHOH$, $-SO_3H$, $-SO_2CH_3$, $-SO_2NHR^{22}$, $-O(CH_2)_mOR^{23}$, $-C(OH)=N(OH)$, $-C(O)NR^{24}OH$, $-CHR^{25}N(COR^{26})OH$, or $-C(O)R^{27}$ or $R^8$ and $R^9$ together form $-NHC(O)-$, $-C(O)NH-$, $-C(O)O-$, $-O-$, $-NR^{29}-$, or $-S(O)_2NH-$;

$R^8$ is $NH_2$;

X is absent or is $-O-$, $-NR^{28}-$, or $-S-$;

$R^{13}$, $R^{14}$, $R^{15}$, $R^{16}$, $R^{17}$, $R^{22}$, $R^{23}$, $R^{24}$, $R^{25}$, $R^{26}$, $R^{28}$, and $R^{29}$ are each independently hydrogen, alkyl, aryl, or cycloalkyl and $R^{27}$ is alkyl, aryl, or cycloalkyl; and n and m are independently 0, 1, 2, 3, 4, 5, or 6.

In other embodiments, the invention is directed to a compound represented by the formula:

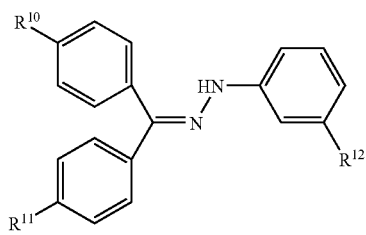

wherein $R^{10}$, $R^{11}$, and $R^{12}$ are each independently hydrogen, alkyl, hydroxyl, alkoxy, $-NR^{13}R^{14}$, halo, nitro, cyano, borono, aryl, aryloxy, $-(CH_2)_nCOOR^{15}$, $-O(CH_2)_nCOOR^{16}$, $-OC(O)R^{17}$, $-CR^{18}=NOH$, $-CR^{19}R^{20}NHOH$, $-SO_3H$, $-SO_2R^{21}$, $-SO_2NHR^{22}$, $-O(CH_2)_mOR^{23}$, $-C(OH)=N(OH)$, $-C(O)NR^{24}OH$, $-CHR^{25}N(COR^{26})OH$, or $-C(O)R^{27}$;

$R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, and $R^{26}$ are each independently hydrogen, alkyl, or aryl and $R^{27}$ is alkyl or aryl; and n and m are independently 0, 1, 2, 3, 4, 5, or 6.

In certain embodiments, the invention is directed to a compound that is a tumor necrosis factor receptor 1 (TNF-R1) inhibitor that binds to an allosteric site of TNF-R1 with an affinity of 1000 nM or greater affinity, preferably 100 nM or greater affinity, and more preferably of 10 nM or greater affinity.

In certain embodiments, the invention is directed to one of the aforementioned compounds, or a compound different from the aforementioned compounds, that exhibits an affinity for wild type TNF-R1 that is at least about 10-fold greater than the affinity the compound exhibits for TNF-R1 bearing a substitution of an amino acid selected from the group consisting of K35, G36, C55, E56, S57, G58, S59, F60, T61, A62, S63, C70, L71, S72, C73, S74, K75, C76, R77, K78, E79, M80, G81, Q82, V83, E84, I85, V90, D91, R92, D93, T94, V95, C96, G97, C98, R99, K100, N101, Q102, Y103, R104, H105, Y106, S108, E109, N110, L111, F112, Q113, C114, F115, Q130, E131, K132, and Q133.

In certain embodiments, the invention is directed to a TNF-R1 inhibitor compound that: (i) binds to an allosteric site of TNF-R1 with an affinity of 100 nM or greater affinity; and (ii) reduces the TNF-α mediated activation of NF-κB and p38 kinase when administered to a cell, compared to the TNF-α mediated activation of NF-κB and p38 kinase activity obtained in said cell when said compound is not administered to said cell.

In other embodiments, the invention is directed to compounds as described above, with the proviso the compound is not a compound of Formula I

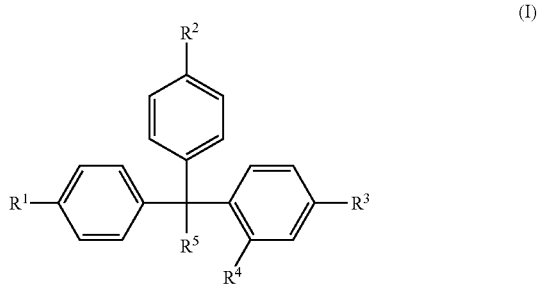

wherein $R^1$ and $R^2$ are independently hydrogen, methoxy, saturated alkyl, 3-carboxy-4-chlorophenylamino, $-N(CH_2CH_2OH)_2$, or OC(O)Ph, $R^3$ is hydrogen, ethyl, methoxy, halogen, t-butyl, carboxy-4-chlorophenylamino, $-N(CH_2CH_2OH)_2$, or OC(O)Ph, $R^4$ is halogen, and $R^5$ is hydrogen.

In other embodiments, the invention is directed to a compound represented by a formula (I), (II), or (III), or a pharmaceutically acceptable salt thereof:

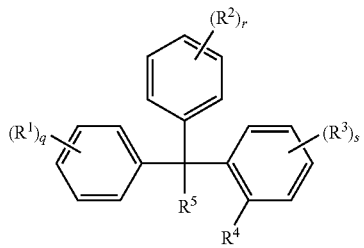

(I)

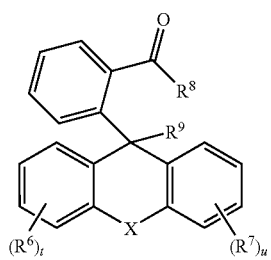

(II)

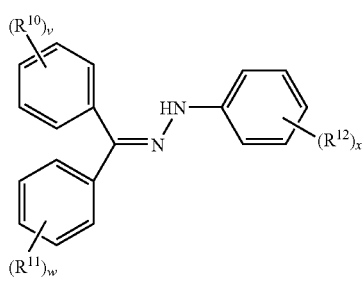

(III)

wherein $R^1$, $R^2$, $R^3$, $R^4$, $R^5$, $R^6$, $R^7$, $R^8$, $R^9$, $R^{10}$, $R^{11}$, and $R^{12}$ are each independently alkyl, hydroxyl, alkoxy, —$NR^{13}R^{14}$, halo, nitro, cyano, borono, aryl, aryloxy, —$(CH_2)_nCOOR^{15}$, —$O(CH_2)_nCOOR^{16}$, —$OC(O)R^{17}$, —$CR^{18}$=NOH, —$CR^{19}R^{20}$NHOH, —$SO_3H$, —$SO_2R^{21}$, —$SO_2NHR^{22}$, —$O(CH_2)_mOR^{23}$, —C(OH)=N(OH), —$C(O)NR^{24}$OH, —$CHR^{25}N(COR^{26})$OH, or —$C(O)R^{27}$ or $R^4$ and $R^5$ together form —$NR^{28}C(O)$—, —$C(O)NR^{29}$—, —C(O)O—, or —$S(O)_2NR^{30}$—, or $R^8$ and $R^9$ together form —O—, —NHC(O)—, —C(O)NH—, —C(O)O—, —$NR^{29}$—, or —$S(O)_2$NH—; or $R^8$ and $R^9$ are each independently hydrogen;

$R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{28}$, $R^{29}$, and $R^{30}$ are each independently hydrogen, alkyl, or aryl and $R^{27}$ is alkyl or aryl;

X is absent or is —O—, —$NR^{28}$—, or —S—; and n and m are independently 0, 1, 2, 3, 4, 5, or 6;

q, r, s, t, u, v, w, and x, are independently 0, 1, 2, or 3;

with a first proviso that if $R^4$ is halogen, $R^5$ is hydrogen, and $R^1$ and $R^2$ are independently hydrogen, methoxy, saturated alkyl, 3-carboxy-4-chlorophenylamino, —$N(CH_2CH_2OH)_2$, or OC(O)Ph, then $R^3$ is not hydrogen, saturated alkyl, methoxy, halogen, carboxy-4-chlorophenylamino, —$N(CH_2CH_2OH)_2$, or OC(O)Ph;

and with a second proviso that the compound is not:

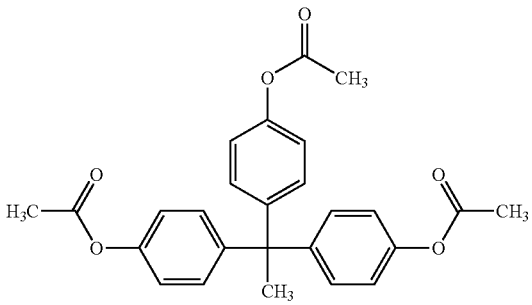

I-9 or a salt thereof.

In yet other embodiments, the invention is directed to a compound represented by the formula, or a pharmaceutically acceptable salt thereof:

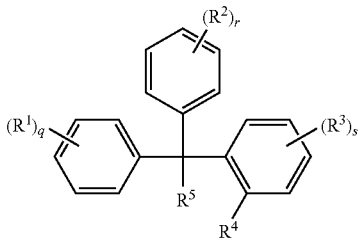

(I)

wherein $R^1$ is —$O(CH_2)_nCOOR^9$ or —$OC(O)CH_2R^{31}$;

$R^2$, $R^3$, $R^4$, and $R^5$ are each independently alkyl, hydroxyl, alkoxy, —$NR^{13}R^{14}$, halo, nitro, cyano, borono, aryl, aryloxy, —$(CH_2)_nCOOR^{15}$, —$O(CH_2)_nCOOR^{16}$, —$OC(O)R^{17}$, —$CR^{18}$=NOH, —$CR^{19}R^{20}$NHOH, —$SO_3H$, —$SO_2R^{21}$, —$SO_2NHR^{22}$, —$O(CH_2)_mOR^{23}$, —C(OH)=N(OH), —$C(O)NR^{24}$OH, —$CHR^{25}N(COR^{26})$OH, or —$C(O)R^{27}$ or $R^4$ and $R^5$ together form —$NR^{28}C(O)$—, —$C(O)NR^{29}$—, —C(O)O—, or —$S(O)_2NR^{30}$—;

$R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{28}$, $R^{29}$, and $R^{30}$ are each independently hydrogen, alkyl, or aryl and $R^{27}$ is alkyl or aryl;

$R^{31}$ is halogen; and n and m are independently 0, 1, 2, 3, 4, 5, or 6;

q, r, and s are each independently 0, 1, 2 or 3 with the proviso that the compound is not:

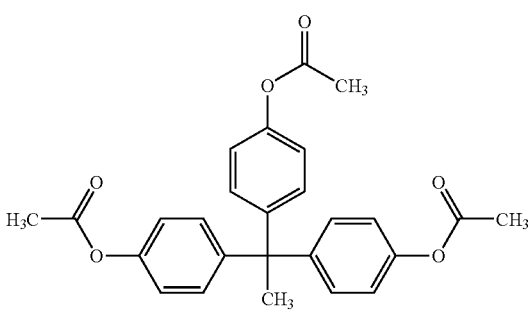

or a salt thereof.

In yet other embodiments, the invention is directed to a compound represented by the formula, or a pharmaceutically acceptable salt thereof:

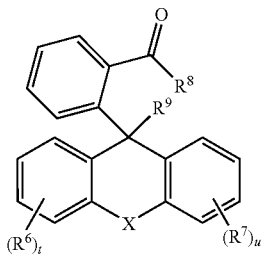
(II)

wherein $R^6$, $R^7$, and $R^9$ are each independently $C_{1-6}$ alkyl, $C_{3-7}$ cycloalkyl, hydroxyl, $C_{1-6}$ alkoxy, —$NR^{13}R^{14}$, halogen, nitro, cyano, borono, phenyl, benzyl, benzoyl, phenoxy, benzyloxy, —$(CH_2)_nCOOR^{15}$, —$O(CH_2)_nCOOR^{16}$, —$OC(O)R^{17}$, —CH=NOH, —$CH_2NHOH$, —$SO_3H$, —$SO_2CH_3$, —$SO_2NHR^{22}$, —$O(CH_2)_mOR^{23}$, —C(OH)=N(OH), —$C(O)NR^{24}OH$, —$CHR^{25}N(COR^{26})OH$, or —$C(O)R^{27}$ or $R^8$ and $R^9$ together form -NHC(O)—, —C(O)NH—, —C(O)O—, —O—, —$NR^{29}$—, or —$S(O)_2NH$—;

or $R^8$ is $NH_2$ or $R^8$ and $R^9$ are each independently hydrogen;

X is absent or is —O—, —$NR^{28}$—, or —S—;

$R^{13}$, $R^{14}$, $R^{15}$, $R^{16}$, $R^{17}$, $R^{22}$, $R^{23}$, $R^{24}$, $R^{25}$, $R^{26}$, $R^{28}$, and $R^{29}$ are each independently hydrogen, alkyl, aryl, or cycloalkyl and $R^{27}$ is alkyl, aryl, or cycloalkyl;

t and u are each independently 0, 1, 2, or 3; and n and m are independently 0, 1, 2, 3, 4, 5, or 6.

In yet other embodiments, the invention is directed to a compound represented by the formula, or a pharmaceutically acceptable salt thereof:

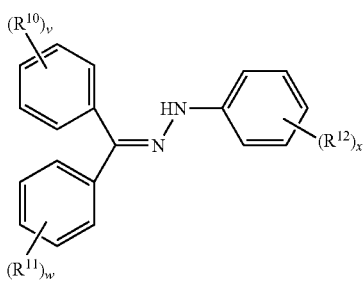
(III)

wherein $R^{10}$, $R^{11}$, and $R^{12}$ are each independently alkyl, hydroxyl, alkoxy, —$NR^{13}R^{14}$, halo, nitro, cyano, borono, aryl, aryloxy, —$(CH_2)_nCOOR^{15}$, —$O(CH_2)_nCOOR^{16}$, —$OC(O)R^{17}$, —$CR^{18}$=NOH, —$CR^{19}R^{20}NHOH$, —$SO_3H$, —$SO_2R^{21}$, —$SO_2NHR^{22}$, —$O(CH_2)_mOR^{23}$, —C(OH)=N(OH), —$C(O)NR^{24}OH$, —$CHR^{25}N(COR^{26})OH$, or —$C(O)R^{27}$;

$R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{25}$ and $R^{26}$ each independently hydrogen, alkyl, or aryl and $R^{27}$ is alkyl or aryl;

v, w, and x, are each independently 0, 1, 2, or 3 and n and m are independently 0, 1, 2, 3, 4, 5, or 6.

In other embodiments, the invention is directed to a pharmaceutical composition comprising a therapeutically effective amount of any of the aforementioned compounds and a pharmaceutically acceptable excipient.

In other embodiments, the invention is directed to methods of treatment of a TNF-α mediated condition, comprising administering an effective amount any of the aforementioned compounds or compositions to a patient in need of such treatment. In other embodiments, the invention is directed to methods of inhibiting tumor necrosis factor action, comprising administering an effective amount of any of the aforementioned compounds or compositions to a patient in need of such treatment. Preferred embodiments of the invention include methods of treating arthritis, inflammation, psoriasis, or an autoimmune condition comprising administering an effective amount of any of the aforementioned compounds or compositions to a patient in need of such treatment.

In yet other embodiments, the invention is directed to use of any of the aforementioned compounds or compositions in the manufacture of a medicament for the therapeutic and/or prophylactic treatment of an autoimmune condition, including conditions such as arthritis, inflammation, and psoriasis.

DETAILED DESCRIPTION

Figure 1:
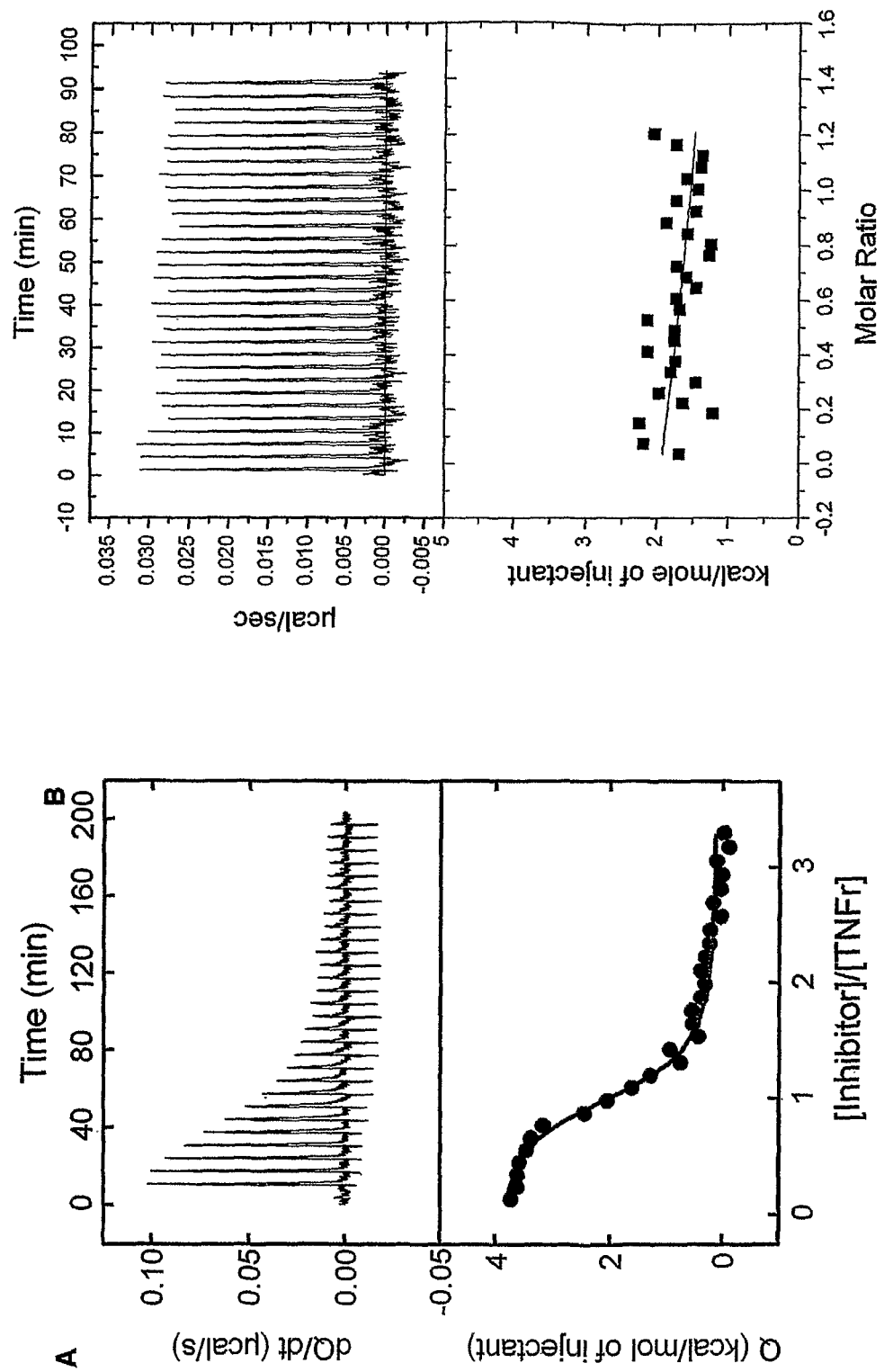
FIG. 1 shows results of isothermal titration calorimetry measurements illustrating the binding of TNF-R1 inhibitor I-9 to (A) recombinant wild type human TNF-R1 receptor and (B) mutant human TNF-R1.

The present inventions are directed to the area of compounds and methods for inhibiting functions mediated by tumor necrosis factor. Such compounds and methods can also be used in treating diseases, disorders, and conditions in which tumor necrosis factor is a participant.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references that are provided throughout this document. The nomenclature used herein and the laboratory procedures in analytical chemistry, and organic synthetic chemistry described below are those well known and commonly employed in the art. Standard techniques, or modifications thereof, are used for chemical syntheses and chemical analyses.

One embodiment of a suitable compound for a pharmaceutical composition is represented by formula (I), or is a pharmaceutically acceptable salt thereof:

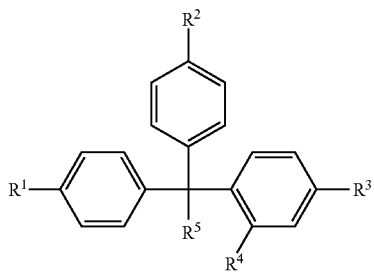

(I)

$R^1$ through $R^5$ can be selected in view of factors such as, for example, affinity, activity, absorption, distribution, metabolism, excretion, pharmacokinetic, toxicological and other properties conducive to their use as pharmaceuticals.

In another embodiment, the compound is represented by formula (I), or is a pharmaceutically acceptable salt thereof, where $R^1$, $R^2$, $R^3$, $R^4$, and $R^5$ are each independently hydrogen, alkyl (preferably, saturated alkyl), hydroxyl, alkoxy, —$NR^{13}R^{14}$, halo, nitro, cyano, borono, aryl, aryloxy, —$(CH_2)_nCOOR^{15}$, —$O(CH_2)_nCOOR^{16}$, —$OC(O)R^{17}$, —$CR^{18}$=NOH, —$CR^{19}R^{20}$NHOH, —$SO_3H$, —$SO_2R^{21}$, —$SO_2NHR^{22}$, —$O(CH_2)_mOR^{23}$, —$C(OH)$=$N(OH)$, —$C(O)NR^{24}OH$, —$CHR^{25}N(COR^{26})OH$, or —$C(O)R^{27}$ or $R^4$ and $R^5$ together form —$NR^{28}C(O)$—, —$C(O)NR^{29}$—, —$C(O)O$—, or —$S(O)_2NR^{30}$—;

$R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{28}$, $R^{29}$, and $R^{30}$ are each independently hydrogen, alkyl (preferably, saturated alkyl), or aryl and $R^{27}$ is alkyl (preferably, saturated alkyl) or aryl; and n and m are independently 0, 1, 2, 3, 4, 5, or 6, with the proviso that if $R^4$ is halogen, $R^5$ is hydrogen, and $R^1$ and $R^2$ are independently hydrogen, methoxy, saturated alkyl, 3-carboxy-4-chlorophenylamino, —$N(CH_2CH_2OH)_2$, or $OC(O)Ph$, then $R^3$ is not hydrogen, saturated alkyl, methoxy, halo, carboxy-4-chlorophenylamino, —$N(CH_2CH_2OH)_2$, or —$OC(O)Ph$.

Examples of such compounds include the following:

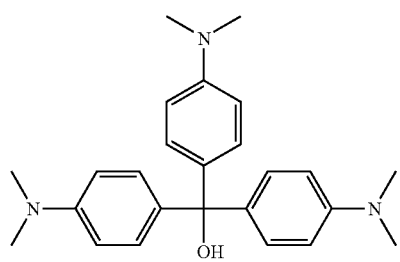

I-1

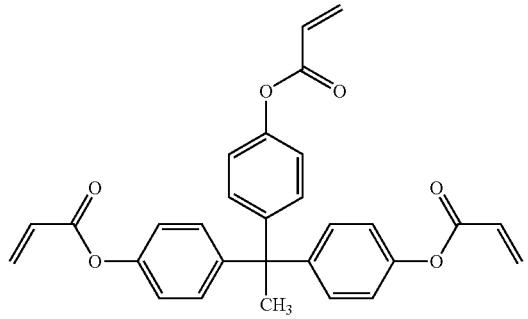

I-2

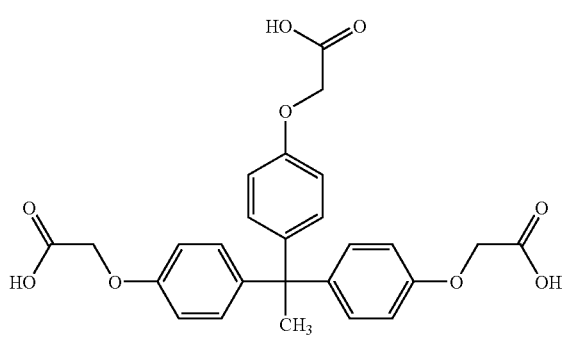

I-3

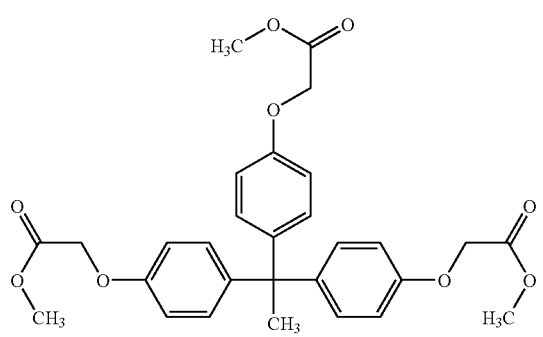

I-4

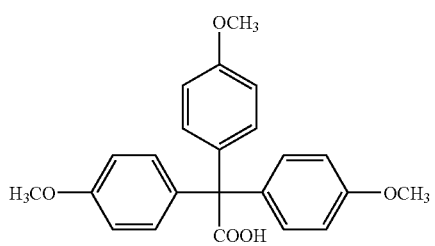

I-5

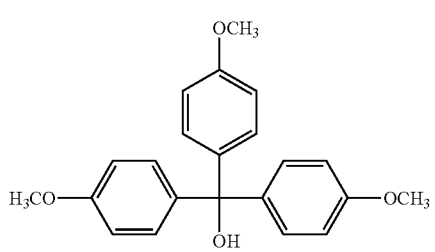

I-6

I-7
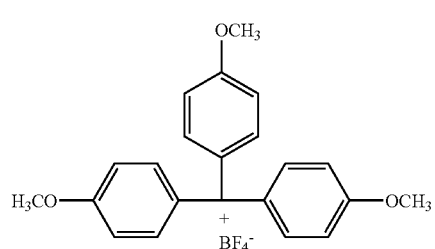
I-8
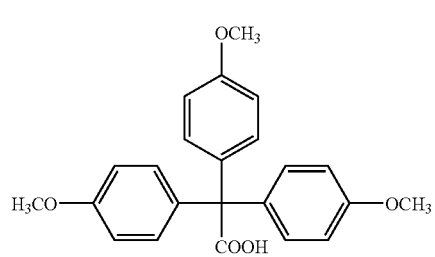
I-9
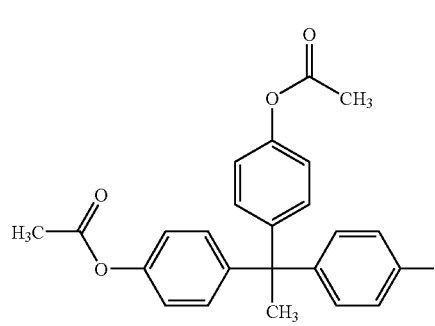
I-10
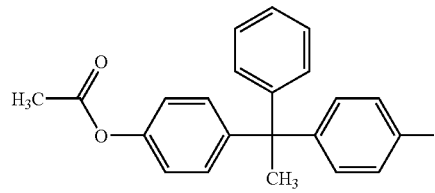
I-11
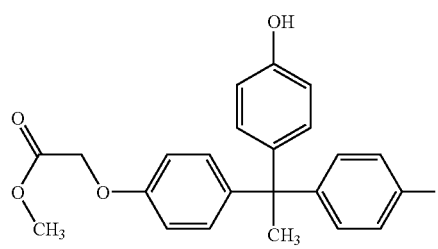
I-12
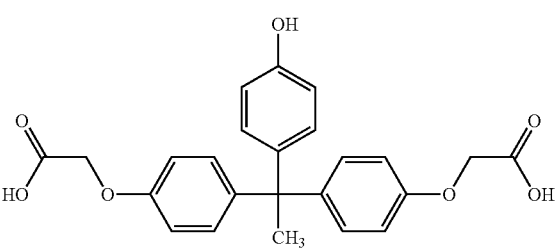
I-13
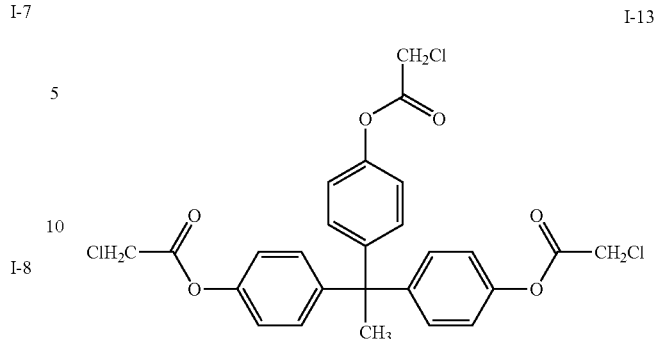
I-14
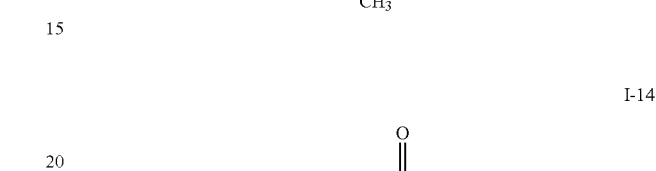
I-15
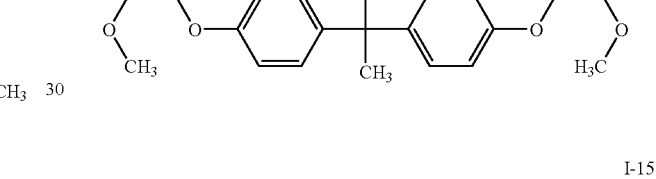
I-16
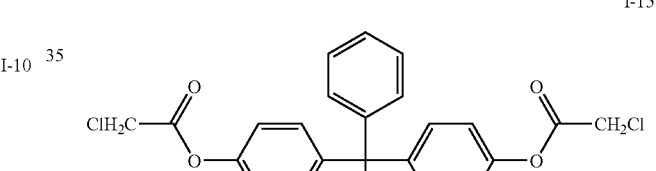
I-17
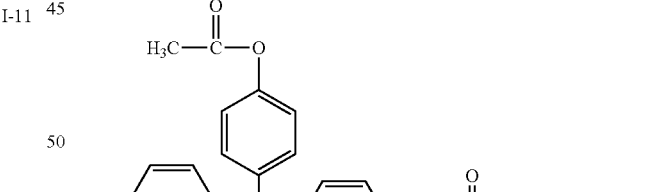

-continued

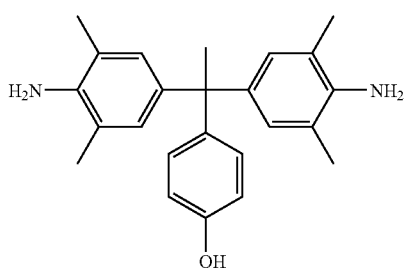

I-18

In another embodiment, the compound is represented by formula (I), or is a pharmaceutically acceptable salt thereof, where $R^1$, $R^2$, $R^3$, $R^4$, and $R^5$ are each independently hydrogen, alkyl (preferably, saturated alkyl), hydroxyl, alkoxy, —$NR^{13}R^{14}$, nitro, cyano, borono, aryl, aryloxy, —$(CH_2)_n COOR^{15}$, —$O(CH_2)_n COOR^{16}$, —$OC(O)R^{17}$, —$CR^{18}$=NOH, —$CR^{19}R^{20}$NHOH, —$SO_3H$, —$SO_2R^{21}$, —$SO_2NHR^{22}$, —$O(CH_2)_m OR^{23}$, —C(OH)=N(OH), —$C(O)NR^{24}$OH, —$CHR^{25}N(COR^{26})$OH, or —$C(O)R^{27}$ or $R^4$ and $R^5$ together form —$NR^{28}C(O)$—, —$C(O)NR^{29}$—, —C(O)O—, or —$S(O)_2NR^{30}$—;

$R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{28}$, $R^{29}$, and $R^{30}$ are each independently hydrogen, alkyl (preferably, saturated alkyl), or aryl and $R^{27}$ is alkyl preferably, saturated alkyl) or aryl; and n and m are independently 0, 1, 2, 3, 4, 5, or 6. Preferably, n and m are 0, 1, or 2.

In yet another embodiment, the compound is represented by formula (I), or is a pharmaceutically acceptable salt thereof, where $R^1$, $R^2$, $R^3$, $R^4$, and $R^5$ are each independently hydrogen, $C_{1-6}$ saturated alkyl, $C_{3-7}$ cycloalkyl, hydroxyl, $C_{1-6}$ alkoxy, —$NR^{13}R^{14}$, nitro, cyano, borono, phenyl, benzyl, benzoyl, phenoxy, benzyloxy, —$(CH_2)_n COOR^{15}$, —$O(CH_2)_n COOR^{16}$, —$OC(O)R^{17}$, —CH=NOH, —$CH_2$NHOH, —$SO_3H$, —$SO_2CH_3$, —$SO_2NHR^{22}$, —$O(CH_2)_m OR^{23}$, —C(OH)—N(OH), —$C(O)NR^{24}$OH, —$CHR^{25}N(COR^{26})$OH, or —$C(O)R^{27}$ or $R^4$ and $R^5$ together form —$NR^{28}C(O)$—, —$C(O)NR^{29}$—, —C(O)O—, or —$S(O)_2NR^{30}$—;

$R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}R^{25}$, $R^{26}$, $R^{28}$, $R^{29}$, and $R^{30}$ are each independently hydrogen, alkyl (preferably, saturated alkyl), or aryl and $R^{27}$ is alkyl (preferably, saturated alkyl) or aryl; and n and m are independently 0, 1, 2, 3, 4, 5, or 6. Preferably, n and m are 0, 1, or 2.

In another embodiment, the compound is represented by formula (I), or is a pharmaceutically acceptable salt thereof, where $R^1$, $R^2$, $R^3$, $R^4$, and $R^5$ are each independently hydrogen, methyl, ethyl, methoxy, —OC(O)H, —$OC(O)CH_3$, —$OC(O)CH_2Cl$, hydroxyl, —$NH_2$, —$N(CH_3)_2$, —OC(O)$CHCH_2$, or —$OCH_2COOCH_3$ or $R^4$ and $R^5$ together form —NHC(O)—.

In yet another embodiment, the compound is represented by formula (I), or is a pharmaceutically acceptable salt thereof, where $R^1$, $R^2$, and $R^3$ are each independently hydrogen, methoxy, —OC(O)H, —$OC(O)CH_3$, —$OC(O)CH_2Cl$, hydroxyl, —$NH_2$, —$N(CH_3)_2$, —OC(O)$CHCH_2$, —$OCH_2COOCH_3$; $R^4$ is hydrogen; and $R^5$ is hydrogen, methyl, —OC(O)H, or hydroxyl or the compound is a pharmaceutically acceptable salt thereof.

In yet another embodiment, the compound is represented by (I), or is a pharmaceutically acceptable salt thereof, where $R^1$ is —$O(CH_2)_n COOR^9$ (for example, —$OCH_2COOCH_3$) or —$OC(O)CH_2Cl$ and $R^2$, $R^3$, $R^4$, $R^5$ and $R^9$ are as defined in the first embodiment of formula (I) above, with the proviso that $R^1$, $R^2$, and $R^3$ are not all —$OCH_2COOCH_3$. Examples of such compounds include compounds I-11, I-12, I-13, I-14, and I-15 above.

In another embodiment, the compound is represented by formula (I), or is a pharmaceutically acceptable salt thereof, where $R^1$ is —$OCH_2COOCH_3$ or —$OC(O)CH_2Cl$, $R^2$ is —$OCH_2COOCH_3$, hydroxyl, or —$OC(O)CH_2Cl$; and $R^3$ is hydrogen, —$OCH_2COOCH_3$, hydroxyl, —$OC(O)CH_3$, or —$OC(O)CH_2Cl$, with the proviso that $R^1$, $R^2$, and $R^3$ are not all —$OCH_2COOCH_3$. Preferably, $R^4$ is hydrogen and $R^5$ is hydrogen, methyl, hydroxyl, or —COOH. Examples of such compounds include compounds having formulas I-11 to I-15.

Other suitable compounds for the pharmaceutical composition include compounds represented by formula (II), or pharmaceutically acceptable salts thereof:

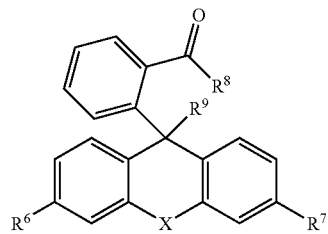

(II)

$R^6$ through $R^9$ can be selected in view of factors such as, for example, affinity, activity, absorption, distribution, metabolism, excretion, pharmacokinetic, toxicological and other properties conducive to their use as pharmaceuticals.

In one embodiment, the compound is represented by formula (II), or is a pharmaceutically acceptable salt thereof, where X is absent or is —O—, —$NR^{28}$—, or —S—; $R^6$, $R^7$, $R^8$, and $R^9$ are each independently hydrogen, alkyl (preferably, saturated alkyl), hydroxyl, alkoxy, —$NR^{13}R^{14}$, halo, nitro, cyano, borono, aryl, aryloxy, —$(CH_2)_n COOR^{15}$, —$O(CH_2)_n COOR^{16}$, —$OC(O)R^{17}$, —$CR^{18}$=NOH, —$CR^{19}R^{20}$NHOH, —$SO_3H$, —$SO_2R^{21}$, $SO_2NHR^{22}$, —$O(CH_2)_m OR^{23}$, —C(OH)=N(OH), —$C(O)NR^{24}$OH, —$CHR^{25}N(COR^{26})$OH, or —$C(O)R^{27}$ or $R^8$ and $R^9$ together form —NHC(O)—, —C(O)NH—, —C(O)O—, —O—, —$NR^{29}$—, or —$S(O)_2NH$—;

$R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{28}$, and $R^{29}$ are each independently hydrogen, alkyl (preferably, saturated alkyl), or aryl and $R^{27}$ is alkyl (preferably, saturated alkyl) or aryl; and n and m are independently 0, 1, 2, 3, 4, 5, or 6.

Examples of such compounds include:

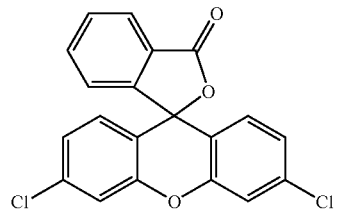

II-1

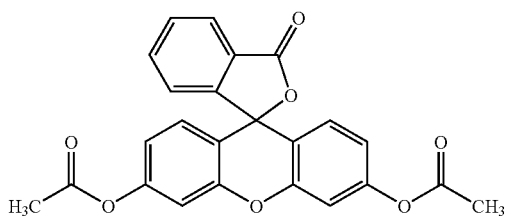

II-2

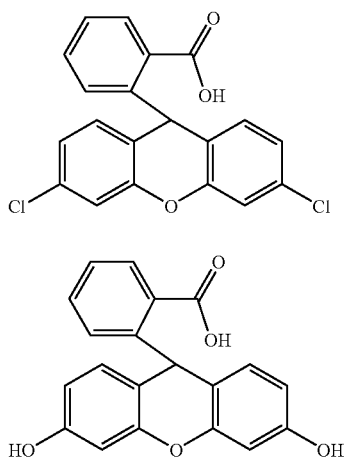

II-3

II-4

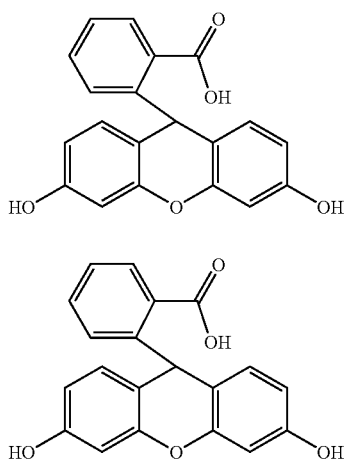

II-5

II-6

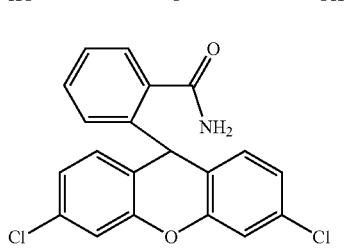

II-7

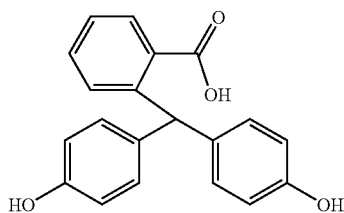

II-8

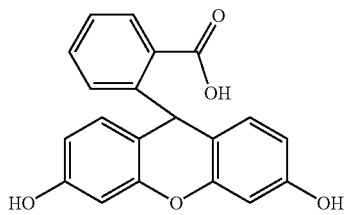

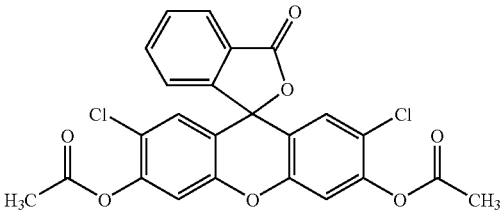

II-9

In another embodiment, the compound is represented by formula (II), or is a pharmaceutically acceptable salt thereof, where X is absent or is —O—, —NR$^{28}$—, or —S—; R$^6$, R$^7$, R$^8$, and R$^9$ are each independently hydrogen, C$_{1-6}$ saturated alkyl, C$_{3-7}$ cycloalkyl, hydroxyl, C$_{1-6}$ alkoxy, —NR$^{13}$R$^{14}$, halogen, nitro, cyano, borono, phenyl, benzyl, benzoyl, phenoxy, benzyloxy, —(CH$_2$)$_n$COOR$^{15}$, —O(CH$_2$)$_n$COOR$^{16}$, —OC(O)R$^{17}$, —CH═NOH, —CH$_2$NHOH, —SO$_3$H, —SO$_2$CH$_3$, —SO$_2$NHR$^{22}$, —O(CH$_2$)$_m$OR$^{23}$, —C(OH)═N(OH), —C(O)NR$^{24}$OH, —CHR$^{25}$N(COR$^{26}$)OH, or —C(O)R$^{27}$ or R$^8$ and R$^9$ together form —NHC(O)—, —C(O)NH—, —C(O)O—, —O—, —NR$^{29}$—, or —S(O)$_2$NH—;

R$^{13}$, R$^{14}$, R$^{15}$, R$^{16}$, R$^{17}$, R$^{22}$, R$^{23}$, R$^{24}$, R$^{25}$, R$^{26}$, R$^{28}$, and R$^{29}$ are each independently hydrogen, alkyl (preferably, saturated alkyl), or aryl and R$^{27}$ is alkyl (preferably, saturated alkyl) or aryl; and n and m are independently 0, 1, 2, 3, 4, 5, or 6. Preferably, n and m are 0, 1, or 2.

In another embodiment, the compound is represented by formula (II), or is a pharmaceutically acceptable salt thereof, where X is absent or is —O—, —NR$^{28}$—, or —S—, R$^6$, R$^7$, R$^8$, and R$^9$ are each independently hydrogen, —C(O)OH, —C(O)OCH$_3$, hydroxyl, —NH$_2$, or halo, or R$^8$ and R$^9$ together form —O—.

In yet another embodiment, the compound is represented by formula (II), or is a pharmaceutically acceptable salt thereof, where X is absent or is —O—, R$^8$ is —NH$_2$ and R$^6$, R$^7$, and R$^9$ are as described above for the first embodiment of compounds of formula (II). Preferably, X is —O—, R$^6$ and R$^7$ are halo, and R$^9$ is hydrogen. An example of such a compound is compound II-6.

In another embodiment, the compound is a pharmaceutically acceptable monovalent salt of a compound having the structure of formula (II) where X is absent or is —O—, R$^8$ is —C(O)OR$^{15}$, R$^6$ and R$^7$ are hydroxyl, and R$^9$ is hydrogen.

Other suitable compounds for use in the pharmaceutical compositions include compounds represented by formula (III), or pharmaceutically acceptable salts thereof:

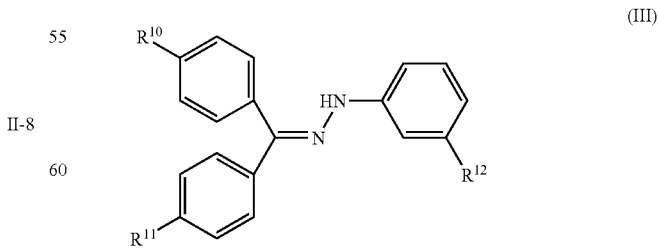

(III)

or pharmaceutically acceptable salts thereof. R$^{10}$ through R$^{12}$ can be selected in view of factors such as, for example, affinity, activity, absorption, distribution, metabolism, excretion, pharmacokinetic, toxicological and other properties conducive to their use as pharmaceuticals.

In one embodiment, the compound is represented by formula (III), or is a pharmaceutically acceptable salt thereof, where $R^{10}$, $R^{11}$, and $R^{12}$ are each independently hydrogen, alkyl (preferably, saturated alkyl), alkoxy, —$NR^{13}R^{14}$, halo, nitro, cyano, borono, aryl, aryloxy, —$(CH_2)_nCOOR^{15}$, —$O(CH_2)_nCOOR^{16}$, —$OC(O)R^{17}$, —$CR^{18}$=NOH, —$CR^{19}R^{20}NHOH$, —$SO_3H$, —$SO_2R^{21}$, —$SO_2NHR^{22}$, —$O(CH_2)_mOR^{23}$, —$C(OH)$=$N(OH)$, —$C(O)NR^{24}OH$, —$CHR^{25}N(COR^{26})OH$, or —$C(O)R^{27}$;

$R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, and $R^{26}$ are each independently hydrogen, alkyl (preferably, saturated alkyl), or aryl and $R^{27}$ is alkyl (preferably, saturated alkyl) or aryl; and n and m are independently 0, 1, 2, 3, 4, 5, or 6.

Examples of such compounds include:

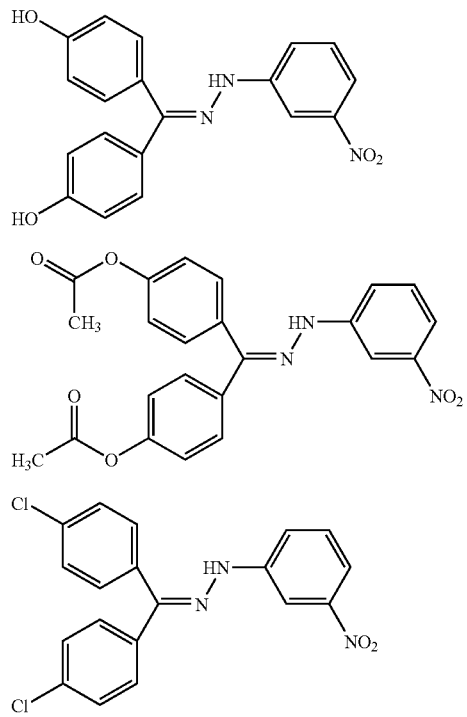

III-1

III-2

III-3

In another embodiment, the compound is represented by formula (III), or is a pharmaceutically acceptable salt thereof, where $R^{10}$, $R^{11}$, and $R^{12}$ are each independently hydrogen, $C_{1-6}$ saturated alkyl, $C_{3-7}$ cycloalkyl, hydroxyl, $C_{1-6}$ alkoxy, —$NR^{13}R^{14}$, halogen, nitro, cyano, borono, phenyl, benzyl, benzoyl, phenoxy, benzyloxy, —$(CH_2)_nCOOR^{15}$, —$O(CH_2)_nCOOR^{16}$, —$OC(O)R^{17}$, —$CH$—$NOH$, —$CH_2NHOH$, —$SO_3H$, —$SO_2CH_3$, —$SO_2NHR^{22}$, —$O(CH_2)_mOR^{23}$, —$C(OH)$=$N(OH)$, —$C(O)NR^{24}OH$, —$CHR^{25}N(COR^{26})OH$, or —$C(O)R^{27}$;

$R^{13}$, $R^{14}$, $R^{15}$, $R^{16}$, $R^{17}$, $R^{22}$, $R^{23}$, $R^{24}$, $R^{25}$, and $R^{26}$ are each independently hydrogen, alkyl (preferably, saturated alkyl), or aryl and $R^{27}$ is alkyl (preferably, saturated alkyl) or aryl; and n and m are independently 0, 1, 2, 3, 4, 5, or 6. Preferably, n and m are 0, 1, or 2.

In another embodiment, the compound is represented by formula (III), or is a pharmaceutically acceptable salt thereof, where $R^{10}$, $R^{11}$, and $R^{12}$ are each independently hydroxyl, —$OC(O)H$, —$OC(O)CH_3$, halo, or nitro.

In yet another embodiment, the compound is represented by formula (III), or is a pharmaceutically acceptable salt thereof, where $R^{12}$ is nitro and $R^{10}$ and $R^{11}$ are hydroxyl, —$OC(O)CH_3$, or halo.

The term "alkyl," by itself or as part of another substituent, means, unless otherwise stated, a straight or branched chain, or cyclic hydrocarbon group (cycloalkyl), or combination thereof, which may be fully saturated, mono- or polyunsaturated and can include di- and multivalent radicals, and can have a number of carbon atoms optionally designated (i.e. $C_1$-$C_{10}$ means one to ten carbons). Examples of saturated hydrocarbon groups include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotonyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups, which are limited to hydrocarbon groups are termed "homoalkyl". Alkyl groups include, for example, $C_{1-6}$ unsubstituted alkyl, $C_{3-7}$ unsubstituted cycloalkyl, trifluoromethyl, chloromethyl, and hydroxymethyl.

The term "heteroalkyl," by itself or in combination with another term, means, unless otherwise stated, a stable straight or branched chain, or cyclic hydrocarbon group, or combinations thereof, consisting of a number of carbon atoms and at least one heteroatom selected from the group consisting of O, N, Si and S, and wherein the nitrogen, carbon and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —$CH$=$CH$—O—$CH_3$, —Si($CH_3$)$_3$, —$CH_2$—$CH$=$N$—$OCH_3$, and —$CH$=$CH$—N($CH_3$)—$CH_3$. Up to two heteroatoms may be consecutive, such as, for example, —$CH_2$—NH—$OCH_3$ and —$CH_2$—O—Si($CH_3$)$_3$.

The term "alkoxy" is used in its conventional sense, and refers to those alkyl groups attached to the remainder of the molecule via an oxygen atom. Alkoxy groups include, but are not limited to, trifluoromethoxy and difluoromethoxy.

The term "cycloalkyl", by itself or in combination with other terms, represents, unless otherwise stated, cyclic versions of substituted or unsubstituted "alkyl" and substituted or unsubstituted "heteroalkyl" ("heterocycloalkyl"). For heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The heteroatoms and carbon atoms of the cyclic structures are optionally oxidized or, in the case of N, quaternized.

The terms "halo" or "halogen," by themselves or as part of another substituent, mean, unless otherwise stated, a fluorine, chlorine, bromine, or iodine atom.

The term "aryl" means, unless otherwise stated, a substituted or unsubstituted polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen, carbon and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. "Aryl" and "heteroaryl" also encompass ring systems in which one or more non-aromatic ring systems are fused, or otherwise bound, to an aryl or heteroaryl system. Aryl-containing groups include, but are not limited to, phenyl, phenoxy, phenoxycarbonyl, benzoyl, benzyl, and benzyloxy.

The term "aryloxy" is used in its conventional sense, and refers to those aryl groups attached to the remainder of the molecule via an oxygen atom.

Each of the above terms (e.g., "alkyl," "heteroalkyl," "aryl" and "heteroaryl") include both substituted and unsubstituted forms of the indicated group, unless indicated otherwise. Preferred substituents for each type of group are provided below.

Substituents for the alkyl groups (including those groups often referred to as heteroalkyl, alkylene, alkenyl, heteroalkylene, heteroalkenyl, alkynyl, cycloalkyl, heterocycloalkyl, cycloalkenyl, and heterocycloalkenyl) are generally referred to as "alkyl substituents" and they can be one or more of a variety of groups selected from, but not limited to: —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$ in a number ranging from zero to (2 m'+1), where m' is the total number of carbon atoms in such group. R', R", R"' and R"" each preferably independently refer to hydrogen, substituted or unsubstituted alkyl including substituted or unsubstituted heteroalkyl, and substituted or unsubstituted aryl, e.g., aryl substituted with 1-3 halogens. When a compound of the invention includes more than one R group, for example, each of the R groups is independently selected as are each of the R', R", R"' and R"" groups when more than one of these groups is present.

Similar to the substituents described for alkyl groups, the aryl substituents are generally referred to as "aryl substituents" and are varied and selected from, for example: halogen, —OR', =O, =NR', —N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R")=NR"', —S(O)R', —S(O)$_2$R', —S(O)$_2$NR'R", —NRSO$_2$R', —CN, —NO$_2$, —R', and —N$_3$, in a number ranging from zero to the total number of open valences on the aromatic ring system; and where R', R", R"' and R"" are preferably independently selected from hydrogen, substituted or unsubstituted alkyl including substituted or unsubstituted heteroalkyl, and unsubstituted aryl. When a compound of the invention includes more than one R group, for example, each of the R groups is independently selected as are each of the R', R", R"' and R"" groups when more than one of these groups is present.

Aryl-containing groups include, but are not limited to, phenyl, phenoxy, phenoxycarbonyl, benzoyl, benzyl, and benzyloxy.

As used herein, the term "heteroatom" includes oxygen (O), nitrogen (N), sulfur (S), boron (B) and silicon (Si).

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Tumor Necrosis Factor Receptor

Tumor necrosis factor (TNF) receptor is one of the central mediators of inflammation. The three dimensional structure of the TNF receptor 1 (TNF-R1) complex has been determined with and without its ligand. Small molecules, described below, can bind to a discrete surface cavity and can disable ligand-induced TNF receptor functions. Although not wishing to be bound by any particular theory, it is thought that this is a consequence of the conformational perturbation of a loop on the receptor containing tryptophan-107 (W107). The conformational perturbation approach identifies surface sites that are relevant for TNF-α, receptor's biological activity in vitro and in vivo.

TNF-R1 is a transmembrane receptor glycoprotein of Mr approximately 55 kDa. The primary translation product of TNF-R1 is modified by cleavage of an amino terminal signal sequence and further by cleavage between arginine and aspartic acid residues found, respectively, approximately 11 and 12 amino acids from the signal sequence cleavage site. A soluble fragment of TNF-R1 of approximately 20 kDa can be isolated from sera and urine. The soluble fragment retains TNF-R1 binding activity. As used herein, the position of amino acids in TNF-R1 are given with reference to the sequence shown in SEQ ID NO: 1.

Although not wishing to be bound by any particular theory, the crystal structure analysis of the TNF receptor complex with and without ligands did not reveal any changes consistent with ligand induced fit. (Banner et al., *Cell* 73, 431 (1993)). Hence the structural role of the ligand was postulated to bring the receptor together and facilitate receptor activation.

Three contact sites (WP5, WP8 and WP9) on TNF-R1 have been identified as contributing to stable ligand complex formation. WP9 (amino acids 105-113) appears to be important for functional interaction with TNF-α. (Takasaki et al., *Nature Biotechnology* 15, 1266 (1997)). A flexible hinge (G81 and G97) identified from the crystal structure analysis was postulated to provide ligand induced conformational changes. Contrary to the result predicted if such a flexible hinge existed, however, no significant conformational changes were observed in the crystallographic complex of TNF-R1/TNF-α versus TNF-R1 alone. Thus, the crystal studies failed to suggest the presence of an allosteric site or cavity on TNF-R1.

Small molecule ligands are identified herein that can be used to induce conformational perturbation at WP9. Identified molecules can then be further selected and modified, if desired, based on their ability to induce conformational changes using molecular simulation studies. Cavities and clefts on the surface of proteins distal to regulatory sites such as ligand binding sites or catalytic sites may be utilized to modulate the function of proteins/receptors by inducing conformational changes as a consequence of lodging small molecules into the cavities. The mode of inhibition can share some features with that of allosteric inhibitors and such small molecules can be referred to as "cavity induced allosteric" inhibitors and the method can be termed as "cavity induced allosteric modification" (CIAM). The target allosteric cavity in TNF-R1 is distal to the W9 contact site and is bounded by a concave surface that can accommodate compounds. The allosteric cavity is bounded by amino acids K35-G36, C55 through S63, C70 through 185, V90 through Y106, S108 through F115 and Q130 through Q133 (see SEQ ID NO: 1).

Treatment of TNF Mediated Conditions

The term "therapeutic agent" is intended to mean a compound that, when present in a therapeutically effective amount, produces a desired therapeutic effect on a mammal. For example, an "effective amount" of a compound for inhibiting tumor necrosis factor action is an amount of a compound or composition that is sufficient to inhibit, reduce, or otherwise mitigate an undesirable effect of tumor necrosis factor action. Such inhibition may occur for example, and without limitation, via a direct interaction, and/or through a competitive interaction, or via an allosteric interaction with TNF-R1, TNF-α, or with another binding protein.

Pharmaceutical compositions containing the small molecules described below can be useful to treat individuals suffering from TNF-mediated diseases, disorders, and conditions. Examples of TNF-mediated diseases, disorders, and conditions include inflammatory diseases and autoimmune diseases such as rheumatoid arthritis (RA), multiple sclerosis (MS), Sjogren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease, ulcerative colitis, Lupus (SLE), Grave's disease, myasthenia gravis, autoimmune hemolytic anemia, autoimmune thrombocytopenia, asthma, cryoglobulinemia, primary biliary sclerosis, pernicious anemia, and periodontal disease (e.g., gingivitis). Individuals suffering from such diseases, disorders, and conditions may be treated by administering to them a therapeutically effective amount of a pharmaceutical composition that contains a compound having Formula I, II, or III or pharmaceutically acceptable salt thereof. Examples of other compounds can be found in U.S. patent application Ser. No. 09/720,647, incorporated herein by reference.

Binding Properties of Compounds

Compounds of the invention bind to TNF-R1. Preferably, compounds bind to TNF-R1 with an affinity (e.g., Id) of 1 μM or less. Without limiting the present disclosure, binding activity may be determined by binding of compounds to cells that express TNF-R1 on their cell surface or a binding of compounds to purified or partially purified TNF-R1. Binding may be determined using, as non-limiting examples, native or recombinant TNF-R1, or fragments thereof. Binding of compounds may be determined using methods that are well known to those skilled in the art. A preferred method for determining binding activity of compounds to TNF-R1 is isothermal titration calorimetry.

In preferred embodiments, a compound exhibits at least about 10-fold greater binding to wild type TNF-R1 or fragment thereof than the binding the compound exhibits for a mutant of TNF-R1 or mutant fragment thereof. More preferred are compounds that exhibit about 100-fold greater binding to TNF-R1 or fragment thereof, compared to the binding the compound exhibits for a mutant of TNF-R1 or mutant fragment thereof. Most preferred are compounds that exhibit about 1000-fold greater binding to TNF-R1 or fragment thereof, compared to the binding the compound exhibits for a mutant of TNF-R1 or mutant fragment thereof.

Further preferred are compounds exhibiting the aforementioned greater binding to wild type TNF-R1 or fragment thereof compared to a corresponding mutant TNF-R1 or fragment thereof, wherein said mutant bears a substitution in an amino acid selected from the group consisting of K35, G36, C55, E56, S57, G58, S59, F60, T61, A62, S63, C70, L71, S72, C73, S74, K75, C76, R77, K78, E79, M80, G81, Q82, V83, E84, I85, V90, D91, R92, D93, T94, V95, C96, G97, C98, R99, K100, N101, Q102, Y103, R104, H105, Y106, S108, E109, N110, L111, F112, Q113, C114, F115, Q130, E131, K132, and Q133. Further preferred are mutants bearing a substitution at Q82 or F112. Most preferred are mutants bearing a substitution at Q82 and F112.

Biological Activity

The activity a compound of the invention can be measured using in vivo or vitro biological assays that measure, for example and without limitation, the ability of a compound to interfere with the biological activity of TNF-α. One example of such an assay is measuring the ability of a compound to inhibit TNF-α mediated cytolysis in L929 cells, or other suitable cells. Other examples of such assays include assaying the ability of a compound to block or inhibit an event associated with intracellular signaling following treatment with TNF-α. Examples of such signaling events include the phosphorylation of NFκB and/or p38 in L929 cells and NE91 cells.

In one embodiment, the biological activity of a compound is measured by the ability of the compound to inhibit TNF-α mediated cytolysis of L929 cells. Compounds of the present invention include compounds that show a 50% inhibition of TNF-α mediated cytolysis of L929 cells at a concentration of 100 μM or less. Other compounds include those that show a 50% inhibition of TNF-α mediated cytolysis of L929 cells at a concentration of 25 μM or less. Still other compounds show a 50% inhibition of TNF-α mediated cytolysis of L929 cells at a concentration of 10 μM or less. Still other compounds show a 50% inhibition of TNF-α mediated cytolysis of L929 cells at a concentration selected from the group consisting of 1 μM or less, 100 nM or less, 10 nM or less, and 1 nM or less.

In another embodiment, the biological activity of a compound is measured by the ability of the compound to inhibit TNF-α-mediated cytolysis in human cell lines such as TMP1, or other suitable human or monkey cell lines.

Salts and Derivatives

Various pharmaceutically acceptable salts, ether derivatives, ester derivatives, acid derivatives, and aqueous solubility altering derivatives of the active compound also are encompassed by the present invention. The present invention further includes all individual enantiomers, diastereomers, racemates, and other isomers of the compound. The invention also includes all polymorphs and solvates, such as hydrates and those formed with organic solvents, of this compound. Such isomers, polymorphs, and solvates may be prepared by methods known in the art, such as by regiospecific and/or enantioselective synthesis and resolution, based on the disclosure provided herein.

Suitable salts of the compound include, but are not limited to, acid addition salts, such as those made with hydrochloric, hydrobromic, hydroiodic, hydrofluoric, perchloric, sulfuric, nitric, phosphoric, acetic, propionic, glycolic, lactic pyruvic, malonic, succinic, maleic, fumaric, malic, tartaric, citric, benzoic, carbonic cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, and 2-acetoxybenzoic acid; salts made with saccharin; alkali metal salts, such as lithium, sodium, and potassium salts; alkaline earth metal salts, such as calcium and magnesium salts; salts formed from Lewis acids, such as boron trifluoride; and salts formed with organic or inorganic ligands, such as quaternary ammonium salts (for example, tris(hydroxymethyl)aminomethane salts).

Additional suitable salts include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate salts of the compound of the present invention.

Prodrugs and active metabolites of compounds disclosed herein are also within the scope of the invention.

A prodrug is a pharmacologically inactive compound that is converted into a pharmacologically active agent by a metabolic transformation or any other chemical or biological process (e.g., hydrolysis). For example, in vivo, a prodrug can be acted on by naturally occurring enzyme(s) resulting in liberation of the pharmacologically active agent. Conventional procedures for the selection and preparation of suitable prodrug derivatives are described, for example, in "Design of Prodrugs," ed. H. Bundgaard, Elsevier, 1985.

An active metabolite is a compound that results from metabolism of another compound after administration of the latter to a subject. Metabolites can be identified by techniques well-known in the art.

Formulation and Administration

Suitable dosage forms include but are not limited to oral, rectal, sub-lingual, mucosal, nasal, ophthalmic, subcutaneous, intramuscular, intravenous, transdermal, spinal, intrathecal, intra-articular, intra-arterial, sub-arachinoid, bronchial, lymphatic, and intra-uterille administration, and other dosage forms for systemic delivery of active ingredients. In a preferred embodiment, the dosage form is suitable for oral administration.

To prepare such pharmaceutical dosage forms, one or more of the aforementioned compounds of formulae (I), (II), or (III), or a pharmaceutically acceptable salt thereof, are intimately admixed with a pharmaceutical carrier according to conventional pharmaceutical compounding techniques. The carrier may take a wide variety of forms depending on the form of preparation desired for administration.

For parenteral formulations, the carrier will usually comprise sterile water, though other ingredients, for example, ingredients that aid solubility or for preservation, may be included. Injectable solutions may also be prepared in which case appropriate stabilizing agents may be employed.

In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like. For solid oral preparations such as, for example, powders, capsules, caplets, and tablets, suitable carriers and additives include starches, sugars, diluents, granulating agents, lubricants, binders, disintegrating agents and the like. Due to their ease in administration, tablets and capsules represent the most advantageous oral dosage unit form. If desired, tablets may be sugar coated or enteric coated by standard techniques.

In some applications, it may be advantageous to utilize the active agent in a "vectorized" form, such as by encapsulation of the active agent in a liposome, micelle, or other encapsulant medium, or by fixation of the active agent, e.g., by covalent bonding, chelation, assembly, or associative coordination, on a suitable biomolecule, such as those selected from proteins, lipoproteins, glycoproteins, and polysaccharides.

Treatment methods of the present invention using formulations suitable for oral administration may be presented as discrete units such as capsules, cachets, tablets, or lozenges, each containing a predetermined amount of the active ingredient as a powder or granules. Optionally, a suspension in an aqueous liquor or a non-aqueous liquid may be employed, such as a syrup, an elixir, an emulsion, or a draught.

A tablet may be made by compression or molding, or wet granulation, optionally with one or more accessory ingredients. Compressed tablets may be prepared by compressing in a suitable machine, with the active compound being in a free-flowing form such as a powder or granules which optionally is mixed with a binder, disintegrant, lubricant, inert diluent, surface active agent, or discharging agent. Molded tablets comprised of a mixture of the powdered active compound with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration usually comprise a sterile aqueous preparation of the active compound, which preferably is isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Parenteral administration may comprise any suitable form of systemic delivery or delivery directly to the CNS. Administration may for example be intravenous, intra-arterial, intrathecal, intramuscular, subcutaneous, intramuscular, intra-abdominal (e.g., intraperitoneal), etc., and may be effected by infusion pumps (external or implantable) or any other suitable means appropriate to the desired administration modality.

Nasal and other mucosal spray formulations (e.g., inhalable forms) can comprise purified aqueous solutions of the active compounds with preservative agents and isotonic agents. Such formulations are preferably adjusted to a pH and isotonic state compatible with the nasal or other mucous membranes. Alternatively, they can be in the form of finely divided solid powders suspended in a gas carrier. Such formulations may be delivered by any suitable means or method, e.g., by nebulizer, atomizer, metered dose inhaler, or the like.

Formulations for rectal administration may be presented as a suppository with a suitable carrier such as cocoa butter, hydrogenated fats, or hydrogenated fatty carboxylic acids.

Transdermal formulations may be prepared by incorporating the active agent in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, formulations of this invention may further include one or more accessory ingredient(s) selected from diluents, buffers, flavoring agents, binders, disintegrants, surface active agents, thickeners, lubricants, preservatives (including antioxidants), and the like. Such pharmaceutical compositions can be prepared by methods and contain carriers which are well-known in the art. A generally recognized compendium of such methods and ingredients is Remington: The Science and Practice of Pharmacy, Alfonso R. Gennaro, editor, 20th ed. Lippingcott Williams and Wilkins: Philadelphia, Pa., 2000.

The formulation of the present invention can have immediate release, sustained release, delayed-onset release or any other release profile known to one skilled in the art.

The subject receiving the pharmaceutical composition is preferably an animal, including, but not limited to, an animal such a cow, horse, sheep, pig, chicken, turkey, quail, cat, dog, mouse, rat, rabbit, and guinea pig, and is more preferably a mammal, and most preferably a human.

The amount of the active agent to be administered can typically range from between about 0.01 to about 25 mg/kg/day, preferably from between about 0.1 to about 10 mg/kg/day and most preferably from between about 0.2 to about 5 mg/kg/day. It will be understood that the pharmaceutical formulations of the present invention need not necessarily contain the entire amount of the agent that is effective in treating the disorder, as such effective amounts can be reached by administration of a plurality of doses of such pharmaceutical formulations.

In a preferred embodiment of the present invention, the compounds are formulated in capsules or tablets, preferably containing 25 to 200 mg of the compounds of the invention, and are preferably administered to a patient at a total daily dose of about 0.5 mg to about 2 g, preferably about 7.5 mg to about 750 mg, more preferably about 15 mg to 750 mg, and most preferably from about 50 to about 200 mg.

A pharmaceutical composition for parenteral administration contains from about 0.01% to about 100% by weight of the active agents of the present invention, based upon 100% weight of total pharmaceutical composition.

EXAMPLES

The following examples illustrate the invention, but are not limiting.

Synthesis of Select Compounds 1,1,1-Tris-(4-carboxymethoxyphenyl)ethane, trisodium salt of I-3

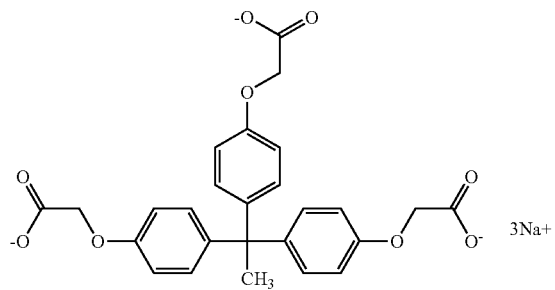

Aqueous sodium hydroxide (3 mL of 0.1 N, 0.3 mmol) was added to a solution of 1,1,1-tris-(4-carboxymethoxyphenyl)ethane (48 mg, 0.1 mmol, made according to Hayakawa, T., et al., *Polymer J.*, 2000, 32(9), 784) in 10 mL of ethanol and the mixture was stirred for 2 h at room temperature. The mixture was evaporated to dryness under reduced pressure to give 55 mg (100% yield) of the desired compound as a white solid, mp>300° C. $^1$H NMR (300 MHz, $D_2O$): δ 1.85 [s, 3H, —$CH_3$], 4.18 [s, 2H, —$OCH_2$—], 6.67 [d, 2H, J=7.7 Hz, Ar—H], 6.83 [d, 2H, J=7.7 Hz, Ar—H].

1,1-Bis-(4-hydroxyphenyl)-1-(4-methoxycarbonyl-methoxyphenyl)ethane (I-11)

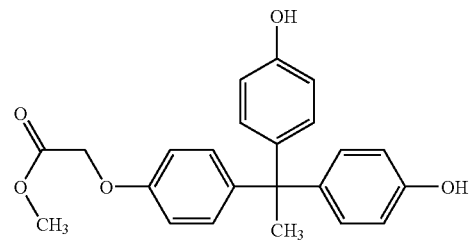

Methyl bromoacetate (0.48 mL, 5 mmol) was added dropwise to an acetone solution (10 mL) including 1,1,1-tris(4-hydroxyphenyl)ethane (1.53 g, 5 mmol) potassium carbonate (0.79 g, 5 mmol) and potassium iodide (16 mg, 0.1 mmol). The addition was done at room temperature under argon. The mixture was refluxed for 24 h, and then it was cooled to room temperature and extracted with ethyl acetate. The combined organic layer was washed with 3% aqueous $NaHCO_3$, a saturated brine solution, dried ($Na_2SO_4$) and then evaporated to dryness to give 1.61 g (85% yield) of the desired compound as a colorless semisolid. $^1$H-NMR (300 MHz, $d_6$-DMSO): 1.96 [s, 3H, —$CH_3$], 3.67 [s, 3H, —$OCH_3$], 4.71 [s, 4H, —$OCH_2$—], 6.57-6.64 [m, 4H, Ar—H], 6.72-6.81 [m, 6H, Ar—H], 6.85-6.92 [m, 2H, Ar—H].

1,1-Bis-(4-carboxymethoxy-phenyl)-1-(4-hydroxyphenyl)ethane, trisodium salt of I-12

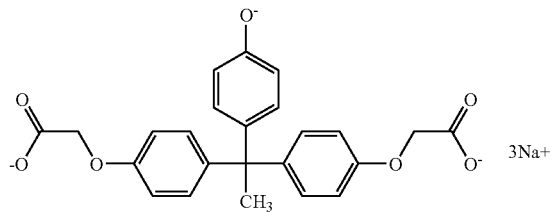

In step (i), methyl bromoacetate (0.95 mL, 10 mmol) was added dropwise to a solution of 1,1,1-tris(4-hydroxyphenyl)ethane (1.53 g, 5 mmol), potassium carbonate (1.38 g, 10 mmol) and potassium iodide (16 mg, 0.1 mmol) in 10 mL of acetone at room temperature under argon. The mixture was refluxed for an additional 24 h; after cooling to room temperature the solution was extracted with ethyl acetate. The combined organic layer was washed with 3% aqueous $NaHCO_3$, saturated brine solution, dried ($Na_2SO_4$) and then evaporated to dryness to afford a solid, which was used without further purification in step (ii).

In step (ii), 0.1 N aqueous sodium hydroxide (9 mL, 0.9 mmol) was added to a solution of 132 mg of the product from step (i) in 5 mL of methanol and the mixture was stirred for an additional 2 h at room temperature. The precipitate was filtered, rinsed with cold ethanol and dried to give 133 mg (91% yield) of the desired compound as a white solid, mp>300° C. $^1$H NMR (300 MHz, $D_2O$): δ 1.77 [s, 3H, —$CH_3$], 4.20 [s, 4H, —$OCH_2$—], 6.35 [d, 1H, J=9.5 Hz, Ar—H], 6.54-6.66 [m, 6H, Ar—H], 6.75-6.86 [m, 5H, Ar—H].

1,1,1-Tris-(4-chloroacetoxyphenyl)ethane (I-13)

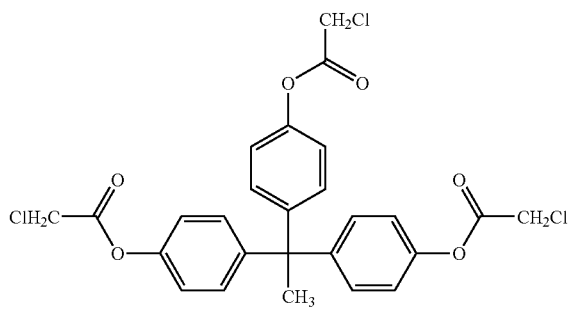

Chloroacetyl chloride (0.12 mL, 1.5 mmol) was added dropwise to an ice cooled solution of 1,1,1-tris(4-hydroxyphenyl)ethane (0.15 g, 0.5 mmol) and triethylamine (0.22 mL, 1.5 mmol) in 10 mL of $CH_2Cl_2$. The mixture was allowed to stand at room temperature overnight. It was then washed with water and saturated brine solution, dried ($Na_2SO_4$) and then concentrated. The residue was recrystallized from ethyl acetate/hexane to give 0.22 g (81% yield) of the desired compound as a white solid, mp: 144-146° C. $^1$H NMR (300 MHz, $d_6$-DMSO): δ2.01 [s, 3H, —$CH_3$], 4.33 [s, 6H, —$CH_2Cl$—], 6.75 [d, 2H, J=8.4 Hz, Ar—H], 6.99 [d, 2H, J=8.4 Hz, Ar—H].

1-(4-Acetoxy-phenyl)-1,1-bis-(4-methoxycarbonyl-methoxyphenyl)ethane (I-14)

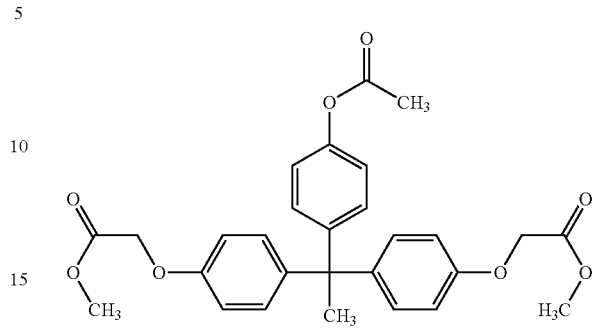

In step (i), methyl bromoacetate (0.95 mL, 10 mmol) was added dropwise to a solution of 1,1,1-tris(4-hydroxyphenyl)ethane (1.53 g, 5 mmol), potassium carbonate (1.38 g, 10 mmol) and potassium iodide (16 mg, 0.1 mmol) in 10 mL of acetone at room temperature under argon. The mixture was refluxed for an additional 24 h, and then it was cooled to room temperature and extracted with ethyl acetate. The combined organic layer was washed with 3% aqueous $NaHCO_3$, saturated brine solution, dried ($Na_2SO_4$) and then evaporated to dryness to afford a solid, which was used without further purification in step (ii).

In step (ii), 0.45 g of the product from step (i) was refluxed with 5 mL of acetic anhydride for 3 h. The volatiles were removed under reduced pressure, and the residue was purified by flash chromatography eluting with hexane-ethyl acetate (1:1) to give 0.43 g (88% yield) of the desired compound as a colorless semisolid. $^1$H-NMR (300 MHz, $CDCl_3$): δ1.57 [s, 3H, —$CH_3$], 2.28 [s, 3H, —$COCH_3$], 3.81 [s, 3H, —$OCH_3$], 4.61 [s, 4H, —$OCH_2$—], 6.75-6.82 [m, 4H, Ar—H], 6.92-7.02 [m, 6H, Ar—H], 7.02-7.10 [m, 2H, Ar—H].

1,1-Bis-(4-chloroacetoxyphenyl)-1-phenylethane (I-15)

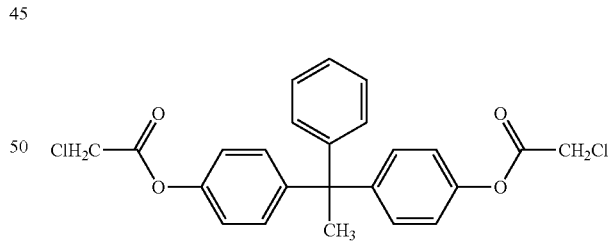

Chloroacetyl chloride (0.08 mL, 1 mmol) was added dropwise to an ice cooled solution of 1,1-bis(4-hydroxyphenyl)-1-phenylethane (0.14 g, 0.5 mmol) and triethylamine (0.15 mL, 1 mmol) in 10 mL of $CH_2Cl_2$. The mixture was allowed to stand at room temperature overnight. It was then washed with water and a saturated brine solution, dried ($Na_2SO_4$) and then concentrated. The residue was recrystallized from ethyl acetate/hexane to give 0.2 g (91% yield) of the desired compound as a white solid, mp: 97-98° C. $^1$H NMR (300 MHz, $d_6$-DMSO): δ2.13 [s, 3H, —$CH_3$], 4.66 [s, 4H, —$CH_2Cl$—], 7.01-7.12 [m, 11H, Ar—H], 7.17-7.23 [m, 1H, Ar—H], 7.25-7.33 [m, 1H, Ar—H].

2-Hydroxy-1,1-bis-hydroxymethyl-ethyl-ammonium; 2-(3,6-dihydroxy-9H-xanthen-9-yl)-benzoate salt of II-5

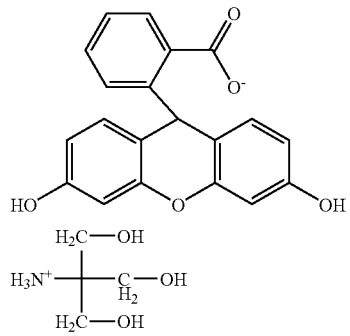

Tris(hydroxymethyl)aminomethane (12 mg, 0.1 mmol) was added to a solution of 2-(3,6-dihydroxy-9H-xanthen-9-yl)-benzoic acid [33 mg, 0.1 mmol, Cui, Y. et al., *Yaoxue Tongbao,* 1982, 17(9), 528] in 5 mL of ethanol and the mixture was stirred for an additional 2 h at room temperature. The mixture was evaporated to dryness under reduced pressure to give 37 mg (100% yield) of the desired compound as an orange colored solid, mp>300° C. $^1$H NMR (300 MHz, D$_2$O): δ3.75 [s, 6H, —CH$_2$—], 5.76 [s, 1H, —CH], 6.94-6.99 [m, 1H, Ar—H], 7.09-7.13 [m, 2H, Ar—H], 7.26-7.31 [m, 6H, Ar—H], 7.49-7.54 [m, 1H, Ar—H].

2-(3,6-Dichloro-9H-xanthen-9-yl)-benzamide (II-6)

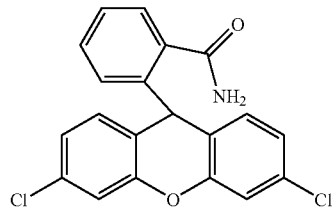

A mixture of 2-(3,6-dichloro-9H-xanthen-9-yl)-benzoic acid (37 mg, 0.1 mmol, Gronowska, J. and Dabkowska-Naskret, H. *Polish J. Chem.,* 1981, 55(10), 2151), thionyl chloride (0.5 mL) and toluene (5 mL) was refluxed for 3 h under argon and concentrated under reduced pressure. Residual thionyl chloride was removed from the crude product mixture by coevaporation with dry CHCl$_3$ (5 mL). Concentrated aqueous NH$_3$ (5 mL) was then added and the mixture stirred overnight at room temperature. The precipitate was filtered, and washed with H$_2$O. The crude product was recrystallized from ethanol to give 33 mg (90% yield) of the desired compound as a white solid, mp 218-220° C. $^1$H NMR (300 MHz, d$_6$-DMSO): δ5.79 [s, 1H, —CH], 6.81-6.86 [m, 1H, Ar—H], 7.04-7.11 [m, 2H, Ar—H], 7.16-7.28 [m, 6H, Ar—H], 7.39-7.45 [m, 1H, Ar—H], 7.76 and 8.23 [s, 2H, NH$_2$].

Potassium 2-[bis-(4-hydroxyphenyl)-methyl]-benzoate salt of II-7

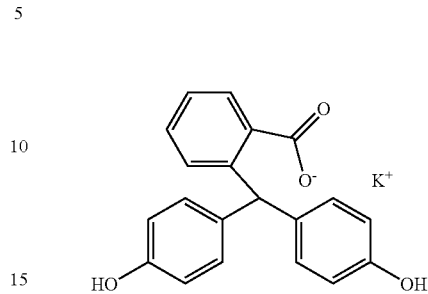

Aqueous potassium hydroxide (1 mL of 0.1 N, 0.1 mmol) was added to a solution of 2-(bis-(4-hydroxyphenyl)-methyl)-benzoic acid [32 mg, 0.1 mmol, Adamczyk, M. and Grote, *J. Organic Preparations and Procedures International,* 2001, 33(1), 95] in 5 mL of ethanol and the mixture was stirred for additional 2 h at room temperature. The mixture was evaporated to dryness under reduced pressure to give 36 mg (100% yield) of the desired compound as a white solid, mp>300° C. $^1$H NMR (D$_2$O, 300 MHz): δ6.41 [s, 1H, —CH], 6.66 [d, 4H, J=8.8 Hz, Ar—H], 6.80 [d, 4H, J=8.8 Hz, Ar—H], 7.03 [d, 1H, J=7.7 Hz, Ar—H], 7.35 [t, 1H, J=7.7 Hz, Ar—H], 7.44 [t, 1H, J=7.7 Hz, Ar—H], 7.74 [dd, 1H, J$_1$=7.7 Hz, J$_2$=2.2 Hz, Ar—H].

Potassium 2-(3,6-dihydroxy-9H-xanthen-9-yl)-benzoate salt of II-8

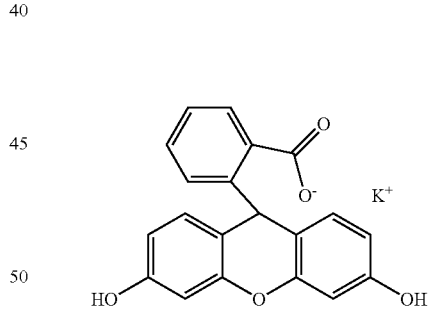

Aqueous potassium hydroxide (1 mL of 0.1 N, 0.1 mmol) was added to a solution of 2-(3,6-dihydroxy-9H-xanthen-9-yl)-benzoic acid [33 mg, 0.1 mmol, Cui, Y. et al., Yaoxue Tongbao, 1982, 17(9), 528] in 5 mL of ethanol and the mixture was stirred for additional 2 h at room temperature. The mixture was evaporated to dryness under reduced pressure to give 37 mg (100% yield) of the desired compound as a orange solid, mp>300° C. $^1$H NMR (D$_2$O, 300 MHz): δ5.76 [s, H, —CH], 6.94-6.99 [m, 1H, Ar—H], 7.09-7.13 [m, 2H, Ar—H], 7.26-7.31 [m, 6H, Ar—H], 7.49-7.54 [m, 1H, Ar—H].

N-(4,4'-Dihydroxybenzhydrylidene)-N'-(3-nitrophenyl)hydrazine (III-1)

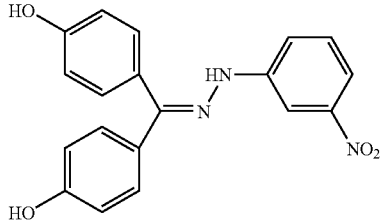

A solution of 4,4'-dihydroxybenzophenone (0.32 g, 1.5 mmol) in 10 mL of methanol was added to a solution of 3-nitrophenylhydrazine hydrochloride (0.43 g, 2.25 mmol), concentrated sulfuric acid (0.3 mL) in 10 mL of methanol at 50° C. It was stirred at 50° C. for additional 2 h. The reaction mixture was concentrated and diluted with 20 mL of water. The precipitates were separated by filtration and washed with 3% aqueous $NaHCO_3$ and water. The crude product was recrystallized from ethanol to give 0.4 g (77% yield) of the desired compound as a yellow solid, mp 160-162° C. $^1$H NMR (300 MHz, $d_6$-DMSO): δ6.71 [d, 2H, J=8.8 Hz, Ar—H], 6.91 [d, 2H, J=8.1 Hz, Ar—H], 7.07 [d, 2H, J=8.8 Hz, Ar—H], 7.27 [d, 2H, J=8.8 Hz, Ar—H], 7.40 [dd, 1H, J=J$_2$=8.1 Hz, Ar—H], 7.49 [d, 1H, J=8.1 Hz, Ar—H], 7.61 [dd, 1H, J$_1$=8.4 Hz, J$_2$=2.2 Hz, Ar—H], 7.99 [d, 1H, J=2.2 Hz, Ar—H], 9.25 [s, 1H, NH], 9.78 and 9.62 [s, 1H, OH].

4,4'-Diacetoxybenzophenone-3-nitrophenylhydrazone (III-2)

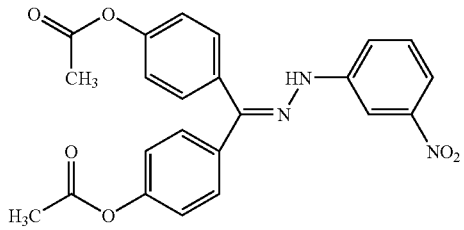

Acetyl chloride (32 μL, 0.41 mmol) was added to an ice cold solution of N-(4,4'-dihydroxybenzhydrylidene)-N'-(3-nitrophenyl)hydrazine (70 mg, 0.2 mol) and triethylamine (60 μL, 0.41 mmol) in 5 mL of $CH_2Cl_2$. The mixture was then allowed to stand at room temperature overnight. It was then washed with water and a saturated brine solution, dried ($Na_2SO_4$) and then concentrated. The residue was recrystallized from ethyl acetate/hexane to give 76 mg (88% yield) of the desired compound as yellow needles, mp: 88-90° C. $^1$H NMR (300 MHz, $d_6$-DMSO): δ2.24 and 2.30 [s, 3H, —$CH_3$], 7.07-7.15 [m, 2H, Ar—H], 7.31-7.40 [m, 4H, Ar—H], 7.42-7.50 [m, 3H, Ar—H], 7.52-7.72 [m, 2H, Ar—H], 7.97-8.05 [m, 1H, Ar—H], 9.56 [s, 1H, NH].

N-(4,4'-Dichlorobenzhydrylidene)-N'-(3-nitrophenyl)hydrazine (III-3)

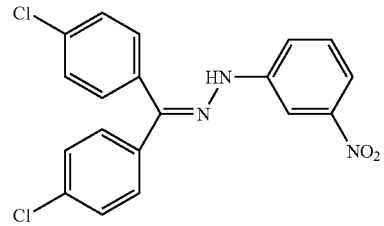

A solution of 4,4'-dichlorobenzophenone (0.38 g, 1.5 mmol) was added to a solution of 3-nitrophenylhydrazine hydrochloride (0.43 g, 2.25 mmol), concentrated sulfuric acid (0.3 mL) in 10 mL of methanol at 50° C. It was stirred at 50° C. for additional 2 h. The reaction mixture was concentrated to ¼ of its original volume and diluted with 20 mL of water. The precipitates were separated by filtration and washed with 3% aqueous $NaHCO_3$ and water. The crude product was recrystallized from ethanol to give 0.46 g (81% yield) of the desired compound as a yellow needle, mp 170-172° C. $^1$H NMR (300 MHz, $d_6$-DMSO): δ7.35 [d, 2H, J=7.7 Hz, Ar—H], 7.37-7.49 [m, 5H, Ar—H], 7.58 [d, 1H, J=8.4 Hz, Ar—H], 7.64 [d, 2H, J=8.4 Hz, Ar—H], 7.69 [d, 1H, J=8.4 Hz, Ar—H], 8.02 [s, 1H, Ar—H], 9.63 [s, 1H, NH].

The following compounds can be prepared according to the indicated references (all of which are incorporated by reference):

1,1,1-Tris-(4-dimethylaminophenyl)methanol (I-1)

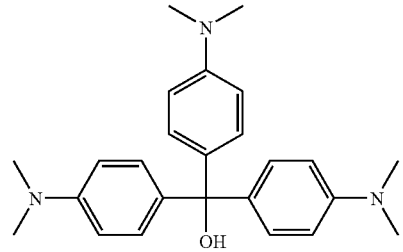

Lohmann, G. Y., U.S. Pat. No. 3,689,495.

1,1,1-Tris-(4-chloroacetoxyphenyl)ethane (I-2)

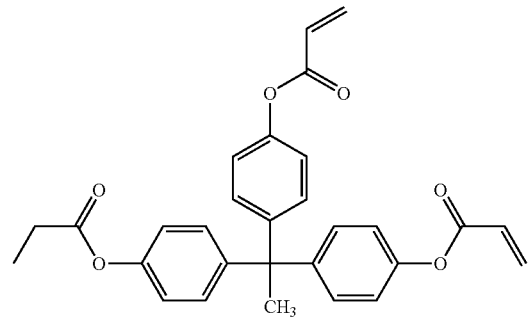

Mott, G. N. and Johnson, T. S. European Patent No. Publication No. 475628.

1,1,1-Tris-(4-methoxycarbonylmethoxyphenyl)ethane (I-4)

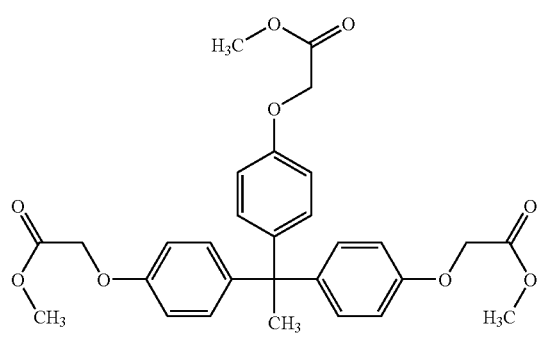

Hayakawa, T., et al., *Polymer J.,* 2000, 32(9), 784.

Sodium 1,1,1-tris-(4-methoxyphenyl)acetate (I-5)

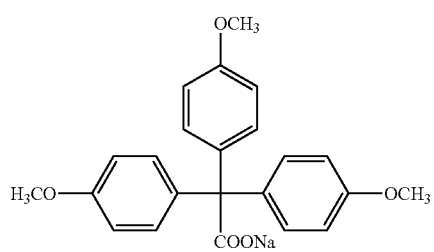

Ford-Moore A. H., *J. Chem. Soc.,* 1962, 1445.

1,1,1-Tris-(4-methoxyphenyl)methanol (I-6)

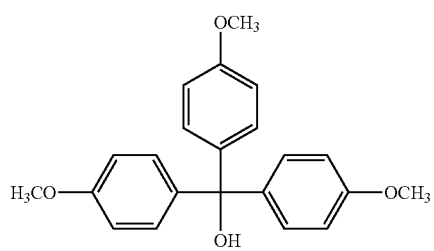

Nixon, A. C. et al., *J. Am. Chem. Soc.,* 1955, 77(11), 3044.

4,4',4''-Trimethoxytrityl tetrafluoroborate (I-7)

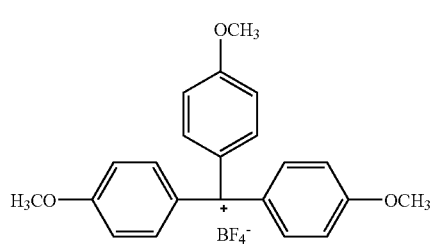

Henderson, A. P., et al., *J. Chem. Soc. Perkin Trans. 1,* 1997, 3407.

1,1,1-Tris-(4-methoxyphenyl)acetic acid (I-8)

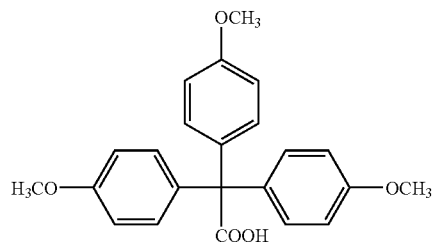

Brain, E. G. et al., *J. Chem. Soc.,* 1962, 1445.

1,1,1-Tris-(4-acetoxyphenyl)ethane (I-9)

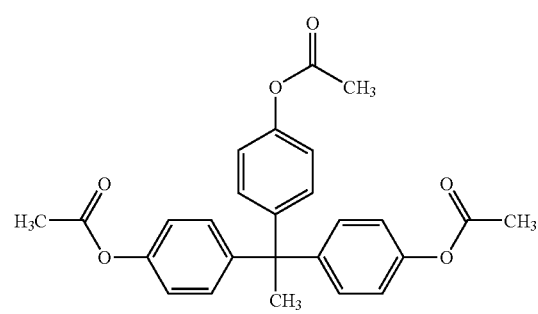

Vicari, R. and Bodman, M. P., U.S. Pat. No. 5,362,843.

1,1-Bis-(4-acetoxyphenyl)-1-phenyl-ethane (I-10)

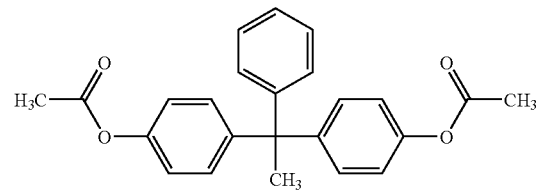

McGreal, M. E. et al., J. Am. Chem. Soc., 1939, 61, 345.

3,3-Bis[4-(acetyloxy)phenyl]-1,3-dihydro-2H-indol-2-one (I-16)

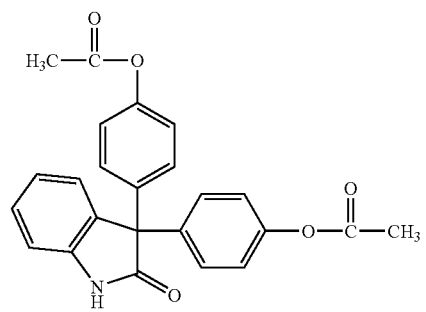

Preiswerk, E., U.S. Pat. No. 1,624,675.

1,1-Bis(4-dimethylaminophenyl)-1-phenyl-methanol (I-17)

Gilman, H. and Jones, R. G., J. Am. Chem. Soc., 1940, 62, 1243.

1,1-Bis(4-amino-3,5-dimethylphenyl)-1-(4-hydroxyphenyl)-ethane (I-18)

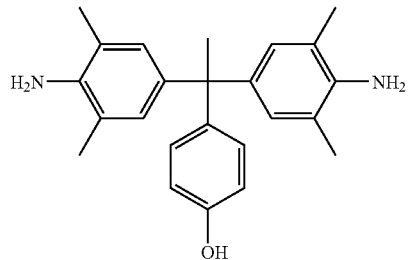

This compound is available from Specs (Netherlands, Cat. No. AG-205/32370012).

3',6'-Dichlorofluorescein (II-1)

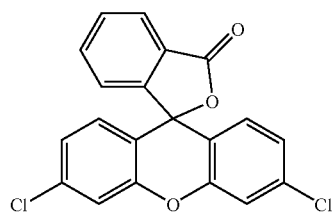

Deno, N. C. and Evans, W. L., J. Am. Chem. Soc., 1957, 79, 5804.

3',6'-Fluorescein diacetate (II-2)

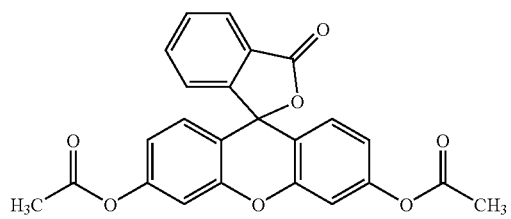

Hurd, C. D. and Schmerling, L., J. Am. Chem. Soc., 1937, 59, 112.

2-(3,6-Dichloro-9H-xanthen-9-yl)-benzoic acid (II-3)

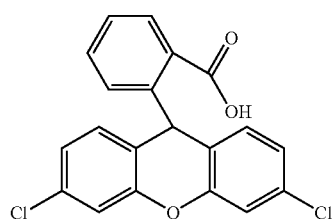

Gronowska, J. and Dabkowska-Naskret, H. Polish J. Chem., 1981, 55(10), 2151.

2-(3,6-Dihydroxy-9H-xanthen-9-yl)-benzoic acid (II-4)

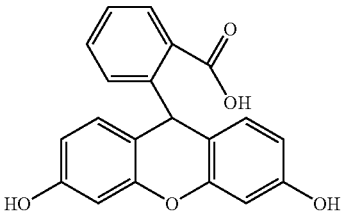

Cui, Y. et al., Yaoxue Tongbao, 1982, 17(9), 528

2',7'-Dichlorofluorescein diacetate (II-9)

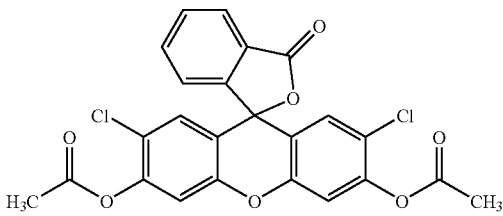

Brandt, R. and Keston, A. S., Anal. Biochem., 1965, 11(1), 6.

Wild Type and Mutant Human TNF Receptor 1 Cloning, Expression and Purification

The ectodomain of wild type TNF receptor 1 was obtained by PCR from pKP13 (as described in Beutler et al., Annu. Rev. Biochem. 57, 505-518 (1988)) with 5' primer AAA AAA CAT ATG TAC CCC TCA GGG GTT ATT GG (SEQ ID NO:2) and 3' primer CCG CTC GAG TCA ATG ATG ATG ATG ATG ATG TGT GGT GCC TGA GTC CTC AG, (SEQ ID NO:3) and constructed into PET21 (Novagen, San Diego, Calif.) between Nde1 and XhoT, verified by sequencing. Mutant TNF receptor 1 was obtained from site-directed mutagenesis by using a QuikChange mutagenesis kit (Stratagene, La Jolla, Calif.). The plasmid was then transformed into Origami™ (DE3) (Novagen, San Diego, Calif.). The cells were grown until A600 was 0.6 and were induced by addition of 0.2 mM of IPTG. The cells were then induced for 3 h and harvested by centrifugation at 3500 rpm for 10 min. The wild type and mutant TNF-R1 were all expressed in the inclusion bodies of the cells and were extracted and refolded as described in Lin et al., Biotechniques 11, 748 (December 1991). Briefly, the cell pellets from 100 mL culture were responded in 5 mL ice-cold buffer A (20 mM Tris-HCl, pH 7.5, 20% Sucrose, 1 mM EDTA) for 10 min, centrifuged at 6000 rpm for 5 min at 4° C., then re-suspended in 50 mL of ice-cold water for 10 min, and centrifuged at 8200 rpm for 5 min at 4° C. The pellet was suspended in 10 mL of Buffer P (PBS containing 5 mM EDTA, 1 mM PMSF, 0.1% Aprotinin) and sonicated. After sonication, the cell suspension were incubated with DNase I (400 µg/10 mL) for 10 min at room temperature. The suspension was further diluted by adding 40 mL of Buffer P and centrifuged at 11,000 rpm for 30 min, 4° C. The pellet was then washed twice with Buffer W (PBS containing 25% Sucrose, 5 mM EDTA, 1% Triton) for 10 min at 4° C. and centrifuged at 15,000 rpm for 10 min, 4° C. The pellet was then resuspended in 10 mL of Buffer U2 (50 mM Tris-Hcl, pH 8.0, 8 M Urea) on ice for 1 h, centrifuged at 11,000 rpm for 30 min at 4° C. The supernatant was added to 1 L of Buffer R (50 mM Tris-HCl, pH8.0, 20% glycerol, 1 mM PMSF, 0.1% Aprotinin) for refolding, stirred gently overnight at 4° C. to renature the protein.

The refolded protein solution was centrifuged at 11,000 rpm for 30 min at 4° C. to remove the aggregation. The supernatant was mixed with Talon metal affinity resin (QIAexpressonst™, Qiagen, Inc, Valencia, Calif.), rocked for 2 h at 4° C., and then washed three times with 50 mM $NaH_2PO_4$ containing 300 mM NaCl and 20 mM imidazole. The purified TNF-R1 was finally eluted with 51 mM $NaH_2PO_4$ containing 300 mM NaCl and 150 mM imidazole, pH 8.0.

Commercially obtained TNF receptor 1 may also be used for any of the examples disclosed herein.

Binding of Allosteric Inhibitor Leads to Perturbation of w107

Compound I-9 was tested for its ability to bind to an isolated and purified TNF-R1. Isothermal titration calorimetry (ITC) was employed to deduce the binding characteristics and the results are shown in FIG. 1. I-9 bound selectively to TNF-R1 at one site with an affinity of $2.2 \times 10^{-6}$ $M^{-1}$.

It appears that there are no large detectable conformational changes on ligand binding (Banner et al., *Cell* 73, 431 (1993)), so it is thought that conformational alterations may be subtle, perhaps on the order of 2 Å (0.2 nm). Fluorescence quenching can identify small modulating changes in proteins. Only one tryptophan residue exists in the TNF-R1 ectodomain and it is located in the WP9 loop.

Figure 2:
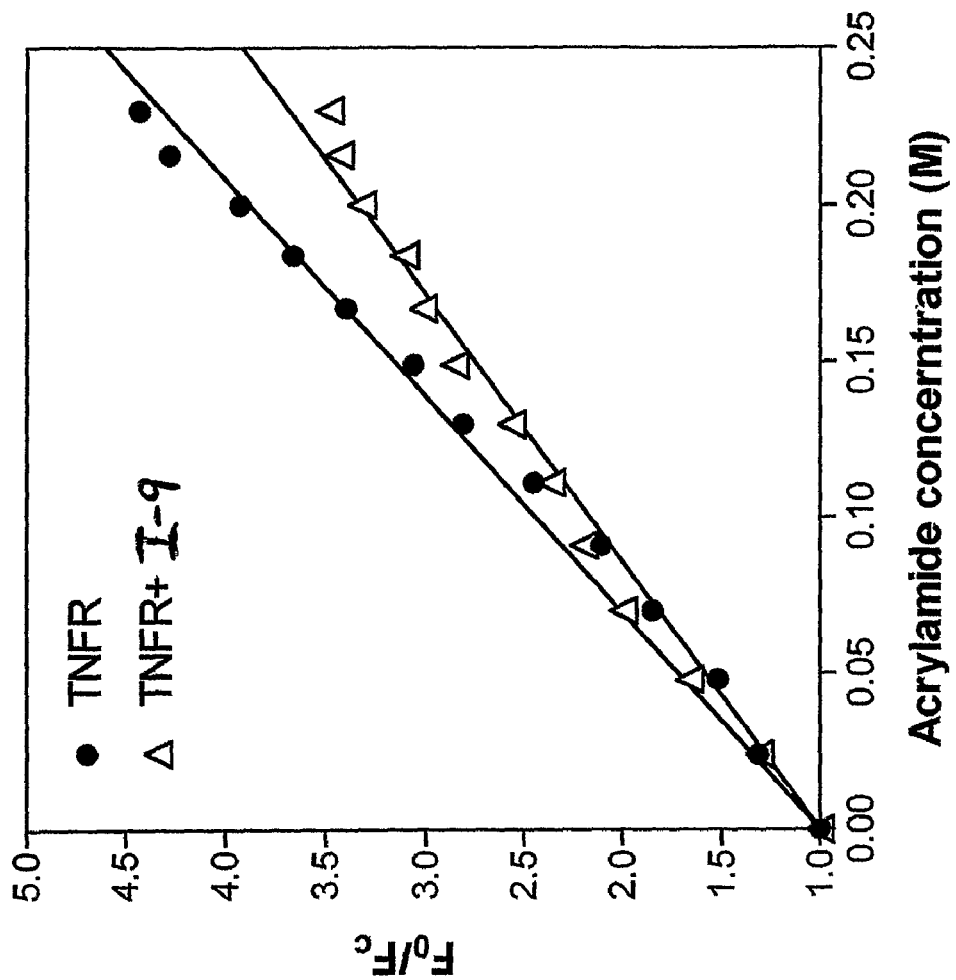
FIG. 2 shows a Stern-Volmer plot for quenching of the intrinsic tryptophan fluorescence of TNF-R1 by acrylamide for TNF-R1 alone (solid circles) and in the presence of TNF-R1 inhibitor I-9 (open triangles).

The results from fluorescence quenching induced by acrylamide following binding of compound I-9 are shown in FIG. 2. The residue W107 in the WP9 loop fluoresces around 340 nm. In this set of experiments, the resultant concentration of quencher ranged up to 0.25 M, quenching 77.4% of the total intrinsic fluorescence of TNF-R1. The Stem-Volmer constant for TNF-R1 quenching by acrylamide calculated from the slope of the plot is $14.4 \pm 0.2$ $M^{-1}$, compared to $11.6 \pm 0.2$ $M^{-1}$ for TNF-R1 in the presence of the test compound, indicating that binding of I-9 to TNF-R1 introduced conformational changes in the TNF-R1 which partly protects W107 from the quencher. Thus binding of I-9 to the receptor changed the disposition of tryptophan-107.

Binding of Allosteric Inhibitor to Mutant TNF-R1

Mutations of the TNF-R1 receptor were made at residues 82Q and 112F in the cavity, which were mutated to 82E and 142E respectively. The structural integrity of the mutant receptor was verified by ligand binding in surface plasmon resonance (SPR) studies. Ligand, TNF-α, bound to the wild type TNF-R1 ($k_d=3.79 \times 10^{-10}$ M) and with mutant TNF-R1 ($k_d=4.65 \times 10^{-6}$ M) suggesting that the mutations affected the ligand binding sites to some extent. Using ITC, it was found that compound I-9 no longer bound to the mutant receptor (FIG. 1B). TNF-α retained the ability to bind to the mutant receptor, albeit with somewhat reduced affinity. These studies confirm that the test compound bound to a single and specific cavity on wild type TNF-R1.

Inhibition of TNF-α-Mediated Cytotoxicity

L929 cultured murine fibroblasts cells were obtained from American Type Culture Collection (Manassas, Va.). Tissue culture reagents were from Invitrogen or Sigma-Aldrich. TNF-α and Actinomycin D were from Sigma-Aldrich. Alamar Blue reagents (Cell Titer Blue™) were from Promega. The test compounds I-1 through I-16, II-1 through II-8, and III-1 through III-3 were obtained commercially or can be prepared as described above. The test compounds were individually dissolved in dimethylsulfoxide (DMSO). The test compounds were maintained at 4° C. when not in use. Other reagents were high-purity (ACS-grade, HPLC-grade, MilliQ water, or similar).

Stock L929 cells were grown on tissue culture plastic in complete DMEM (Dulbecco's Modified Eagles Medium) supplemented with 10% FBS (Fetal Bovine Serum), NEAA (non-essential amino acids), and glutamine. L929 cells were plated using the same medium on 96-well tissue culture plates at high density (i.e., $\sim 4 \times 10^4$ cells/well, or similar) before use.

Approximately 20 h after plating, the L929 cells on 96-well plates were re-fed with fresh medium containing one of the test compounds in a concentration selected from 100 µM, 50 µM, 25 µM as a "pre-treatment." Approximately 30-60 min later, samples were treated with an additional amount of test compound (in the same amount and at the same concentration as the pre-treatment) prepared in medium containing TNF-α (200 pg/mL), and actinomycin D (2 µM). The final concentration of TNF-α in assays was 100 pg/mL. The final concentration of actinomycin D in assays was 1 µM. The plates were incubated for an additional 22-23 h, the Alamar Blue assay reagents were added and metabolic cell viability was determined from reduction of a fluorogenic Alamar Blue derivative.

The temperature was maintained at 37° C. with 5% $CO_2$ and humidified. The metabolic viability was measured 1-2 h after addition of assay reagents/Alamar Blue derivative using TECAN SaFire fluorescence plate reader (Tecan Group Ltd., Maennedorf, Switzerland).

Inhibition of TNF-α induced cytolysis by a test compound (X) at a given concentration (y) was calculated as follows:

$$\% \text{ Inhibition} = 100 * \left\{ \frac{\text{Viability}(X\,y\mu M, ActD\,\&TNF) - \text{Viability}(ActD\,\&TNF)}{\text{Viability}(ActD) - \text{Viability}(ActD\,\&TNF)} \right\}$$

Results for compounds tested in the TNF-α mediated cytolysis assay are given in Table 1.

TABLE 1

Inhibition of TNF-α Mediated Cytolysis of L929 Cells

| | % Inhibition at: | | |
|---|---|---|---|
| Compound | 100 µM | 50 µM | 25 µM |
| I-1 | 40.9 | 63.3 | 44.0 |
| I-2 | 18.1 | 57.4 | 24.9 |
| I-3 | 12.4 | 17.7 | 23.0 |
| I-4 | −11.6 | 27.9 | 18.4 |
| I-5 | 12.1 | 5.0 | 1.7 |
| I-6 | 32.5 | 25.9 | 12.0 |
| I-7 | 25.9 | 30.2 | 15.1 |
| I-8 | 18.4 | 6.9 | 2.7 |
| I-9 | 50.9 | 65.2 | 37.2 |
| I-10 | 71.9 | 46.6 | 20.7 |
| I-11 | 14.8 | 36.7 | 13.9 |
| I-12 | 14.2 | 16.9 | 14.5 |
| I-13 | 38.9 | 72.2 | 35.4 |
| I-14 | 45.3 | 30.2 | 13.4 |
| I-15 | −19.8 | 73.8 | 29.7 |
| I-16 | 17.1 | 11.5 | 4.3 |
| I-17 | −17.9 | −17.0 | −16.0 |
| I-18 | 53.8 | 36.6 | 22.6 |
| II-1 | 7.6 | 8.8 | 20.7 |
| II-2 | 26.0 | 23.5 | 25.4 |
| II-3 | 52.4 | 45.6 | 36.2 |
| II-4 | 23.2 | 23.6 | 33.3 |
| II-5 | 21.5 | 16.3 | 25.1 |
| II-6 | −21.7 | −6.1 | 43.3 |
| II-7 | 13.2 | 19.1 | 22.5 |
| II-8 | 25.6 | 24.7 | 23.6 |
| II-9 | 22.0 | 10.5 | 6.3 |
| III-1 | −20.3 | 42.5 | 33.2 |
| III-2 | −19.8 | 42.0 | 26.9 |
| III-3 | 8.1 | 3.4 | 6.6 |

Inhibition of TNF-α Signaling in L929 Cells

Figure 3:
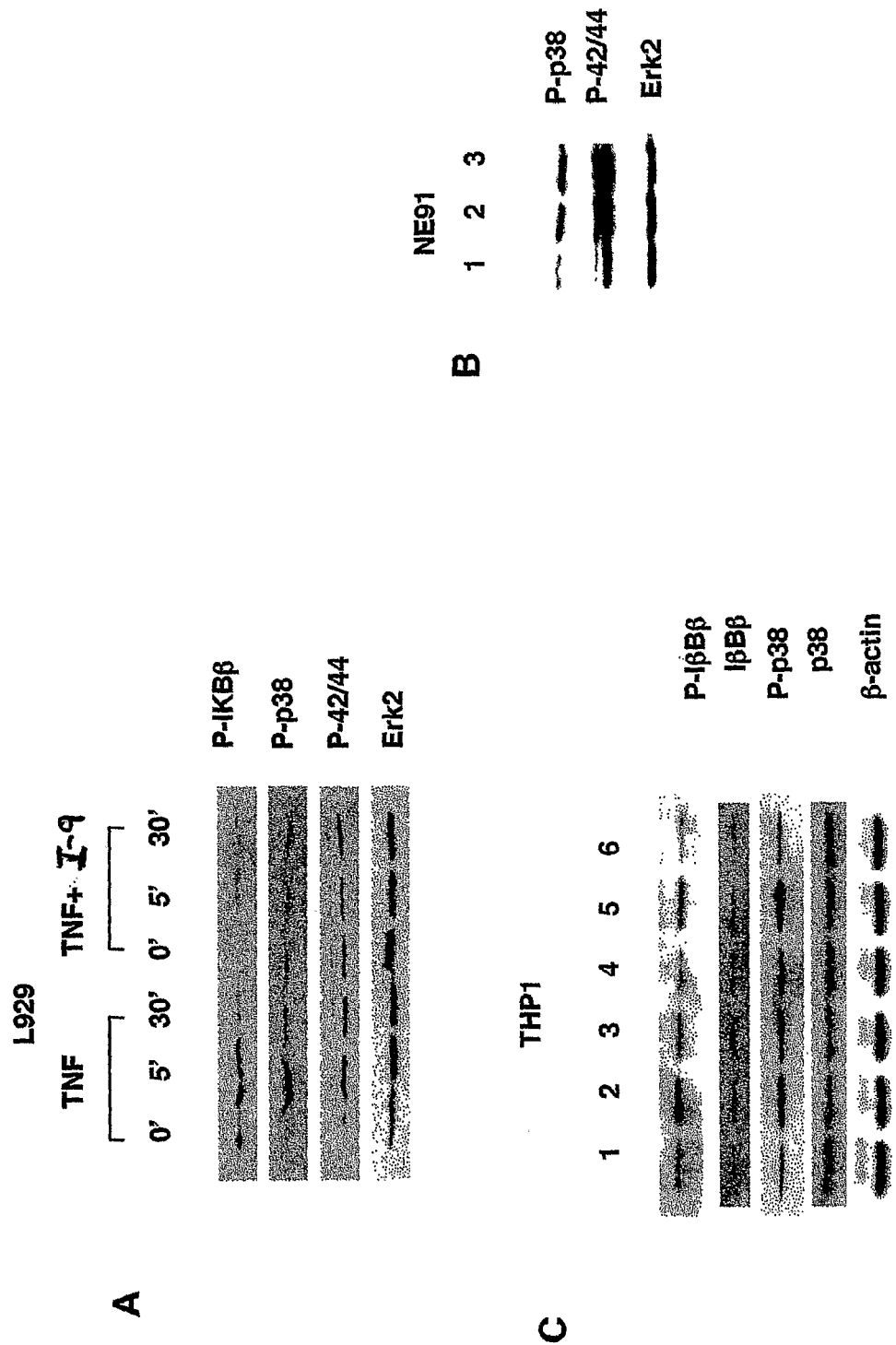
FIG. 3 shows the results of experiments designed to show the effect of TNF-R1 inhibitor I-9 on cell signaling. (A) Effect of I-9 on TNFα-induced phosphorylation of P38 in L929 cells; (B) Effect of I-9 on EGF-induced MAPK activation in NE91 cells; and (C) Effect of I-9 on signaling in THP1. Cells were treated with vehicle (lane 1), LPS (10 ng/mL, lane 2), TNF-α (100 ng/mL, lane 3), inhibitor I-9 (20 µg/mL, lane 4), LPS (10 ng/mL)+inhibitor I-9 (20 µg/mL) (lane 5), and TNF-α (100 ng/mL)+inhibitor I-9 (20 µg/mL) (lane 6).

The effect of compound I-9 on TNF-α signaling was examined in L929 cells (American Type Culture Collection, Manassas, Va.). Cells were cultured in RPMI (Invitrogen) containing 5% fetal bovine serum. Cells ($1 \times 10^6$/well) were cultured in 6-well plates for 12 h, treated with or without small molecule for 2 h, and then stimulated with TNF-α at 20 ng/mL for the indicated periods. Cells were then washed with ice-cold phosphate-buffered saline and lysed with lysis buffer. Cell lysates (15-30 μg) were separated by 12% SDS-PAGE, electroblotted onto nitrocellulose membrane (Osmonics, Westborough, Mass.), and probed with anti-phospho-IκBα, anti-IκBα, anti-phospho-p38, anti-p38, and anti-β-actin antibodies (Cell Signaling Technology, Inc., Beverly, Mass.) and developed using an enhanced chemiluminescence (ECL) system (Amersham Biosciences, Piscataway, N.J.). Results showed that treatment of L929 cells with compound I-9 reduced production of phospho-IκBα and phospho-p38 following TNF-α treatment (FIG. 3A).

Inhibition of TNF-α Signaling in THIP1 Cells

THP1 cells (Human acute monocytic leukemia cell line, American Type Culture Collection, Manassas, Va.) were cultured in RPMI with the supplement of 50 mM HEPES, 1 mM Na Pyruvate, 50 μM of 2-ME, 2.5 mg/mL of glucose, 50 μg/mL of gentamicin and 10% of FBS. Cells were cultured in 12-well plate at a density of $6 \times 10^5$/well with supplement of 100 ng/mL PMA. Cells were plated 72 hrs to differentiate. Cells were then pretreated with or without small molecule for 2 hr, followed by treatment with TNF-α at 20 ng/mL at the indicated periods. Cells were then lysed and analyzed by western blotting in the same manner as described above for L929 cells. Results showed that treatment with compound I-9 inhibited TNF-α mediated I-kBα and p38 phosphorylation in THP1 cells, as shown in FIG. 3C.

Effect on EGF-Signaling in NE91 Cells

To verify the effects of I-9 were specific to TNF-α signaling, the effect of I-9 on EGF-signaling was tested in NE91 cells (American Type Culture Collection, Manassas, Va.). NE91 cells were cultured in RPMI medium containing 10% FBS in 6-well plate at the density of $1 \times 10^6$/well for 12 hr, followed by 2 hr treatment with or without I-9. Cells were then stimulated with EGF at 100 ng/mL for the indicated time. Cells were then lysed and analyzed by western blotting in the same manner as described above for analysis of TNF-α signaling in L929 cells. Results showed that compound I-9 failed to induce changes in EGF-induced signaling (FIG. 3B), indicating that I-9 specifically altered the TNF-R1 signaling pathways.

Inhibition of Collagen Induced Arthritis

Activity of compound I-9 was studied in a mouse collagen induced arthritis system, which is a model for human rheumatoid arthritis. Six to eight weeks old male DBA/1 mice were immunized by multiple intradermal injections of 100 μg chicken type II collagen (Sigma Chemical Co., St. Louis, Mo.) in 100 μl of 0.1 M acetic acid emulsified in an equal volume of complete Freund's adjuvant and were then challenged with the same antigen preparation i.p. on the 21st day. Animals were injected daily with the compound I-9 at different dosages (2-4 mg/kg/day) beginning on day 21 and animals were examined physically every other day in a blinded manner.

Figure 4:
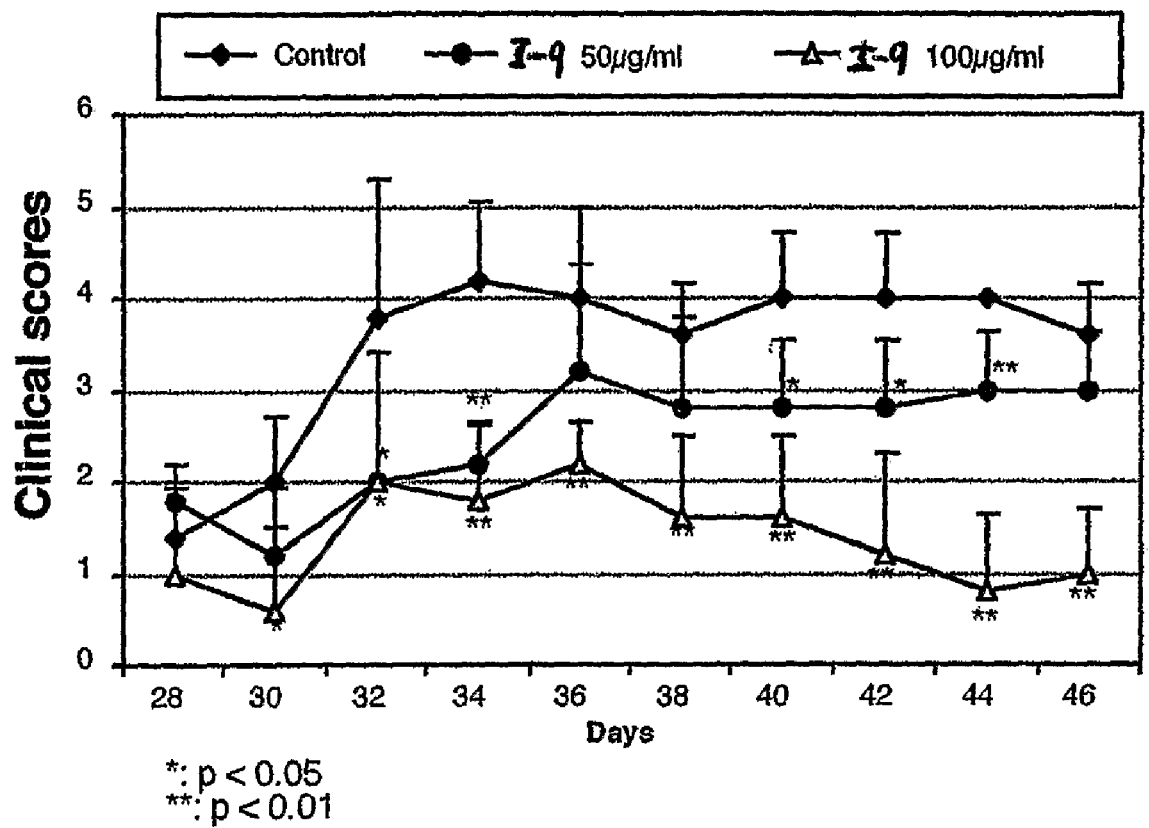
FIG. 4 shows the results of an experiment designed to show the effect of TNF-R1 inhibitor I-9 on collagen induced arthritis in a mouse model of human rheumatoid arthritis. Data are expressed as mean±SEM. Probabilities are results of student t test, from comparisons with control group mice treated with vehicle.

In this model, disease typically develops 7-10 days after the second immunization, and the severity of disease can be determined by physical examination, joint histochemistry, or both techniques. Mice treated with compound I-9 showed a dose dependent decrease in the clinical symptoms of arthritis compared with untreated or control groups (FIG. 4). Histological analysis of ankle joints of the animals revealed that the treated mice have less synovial tissue and reduced matrix proteoglycans. Infiltration was markedly reduced and matrix proteoglycans were not depleted. Cartilage destruction was also prevented in the I-9 treated group.

Effect of TNF Receptor 1 Dependent In Vivo Collagen Induced Arthritis

Male DBA/1 mice (6-8-wk-old) were purchased from Jackson Laboratory (Bar Harbor, Me.) and housed in University of Pennsylvania Animal Care Facilities. Animals were maintained in accordance with guidelines of Institutional Animal Care and Use Committee (IACUC) of the University of Pennsylvania. For CIA induction, mice were immunized by multiple intradermal injections of 100 μg chicken type II collagen (Sigma Chemical Co., St. Louis, Mo.) in 100 μL of 0.1M acetic acid emulsified in an equal volume of complete Freund's adjuvant. Mice were challenged with the same antigen preparation i.p. at the 21st day. Mice were injected daily with the test compound at different dosage (2 and 4 mg/kg of body weight) from day 21. Disease develops 7-10 day after the second immunization. Mice were examined physically every other day in a blind manner. Their paws were scored individually as follows: 0=normal; 1=Erythema and mild swelling confined to the ankle joint or toes; 2=Erythema and mild swelling extending from the ankle to the midfoot or ankle joint; 3=Erythema and moderate swelling extending from the ankle to the metatarsal joints; and 4=Erythema and severe swelling encompass the ankle, foot, and digits. The maximum disease score per foot is 4, and the maximum disease score per mouse is 16. For histological examination of the joint, mice were killed at different time points, and their paws were collected and fixed in 10% formalin. The paws were then decalcified in hydrochloric acid, embedded in paraffin, sectioned, and stained with hematoxylin and eosin (H&E).

Other Methods

Fluorescence Quenching Studies

Quenching experiments with acrylamide were performed in stirred cells, at 25° C., titrating from a stock of 1 M acrylamide by adding 2.5 μl of acrylamide each time. Recombinant TNF-R1 were at the concentration of 5 μM in 1% DMSO. Tryptophan emission, monitored at 340 nm, was observed using 295 nm excitation. Intensity data following quencher additions were averaged over a 10-sec collection and were corrected for background emission (paired control lacking of protein). Intensities, F, at given quencher concentration, [Q], were analyzed using the Stem-Volmer equation, $$F_0/F = 1 + K_{S,V}[Q]$$

Where $F_0$ is the emission intensity of the protein in the absence of quencher, and $K_{S,V}$ is the Stem-Volmer constant for quenching, given by the slope when data are plotted as $F_0/F$ versus [Q].

For synthesized small molecules, a test compound at 20 μM was pre-incubated with 5 μM TNF-R1 in 1% DMSO for 30 min, and titrated with 1 M acrylamide the same way as TNF-R1 alone. The $F_0/F$ was analyzed using the Stem-Volmer equation, and two slopes from TNF receptor and from TNF receptor with the test compound were compared.

Kinetic Binding Studies by Surface Plasmon Resonance

Recombinant TNF receptor wild type and mutant were immobilized to the CM5 sensor chip with a surface density of 2,000 resonance units. The binding affinity of TNF-α to TNF-R1 was estimated by BiaCORE 3000 (BiaCORE, Uppsala, Sweden) at 25° C. The apparent rate constants ($k_{on}$ and $k_{off}$) and the equilibrium binding constant ($K_d$) for TNF/TNF-R binding interaction were estimated from the kinetic analysis of sensorgrams, using the BIA evaluation 3.0 software (BiaCORE).

Isothermal Titration Calorimetry

The binding thermodynamics of inhibitors to the TNF receptor was measured by isothermal titration calorimetry (ITC) using a high-precision VP-ITC titration calorimetric system (MicroCal Inc, Northampton, Mass.). The calorimetric cell containing wild type or mutant TNF receptor at a concentration of about 1 to 6 µM dissolved in 5 mM Tris, pH 8.0 with 2% DMSO, was titrated with the inhibitors dissolved in the same buffer. The concentration of inhibitor was 50-120 µM, depending on the solubility in buffer. Injection volumes were 10 µL. All solutions were properly degassed to avoid any formation of bubbles in the calorimeter during stirring. The heat evolved upon each injection of inhibitor was obtained from the integral of the calorimetric signal. The heat associated with the binding of the inhibitor to TNF receptor was obtained by subtracting the heat of dilution from the heat of reaction. The measurements were made at 25° C. Data were analyzed and fitted using the data analysis software supplied by MicroCal (Origin version 5.0).

\* \* \*

The above specification, examples and data provide a description of the manufacture and use of the composition of the invention. Since many embodiments of the invention can be made without departing from the spirit and scope of the invention, the invention also resides in the claims hereinafter appended.

All references, including publications, patents, and patent applications, cited herein are incorporated herein by reference.

What is claimed:
1. A method of inhibiting tumor necrosis factor action, comprising treating a patient in need of such inhibition with an effective amount of a compound having a structure:
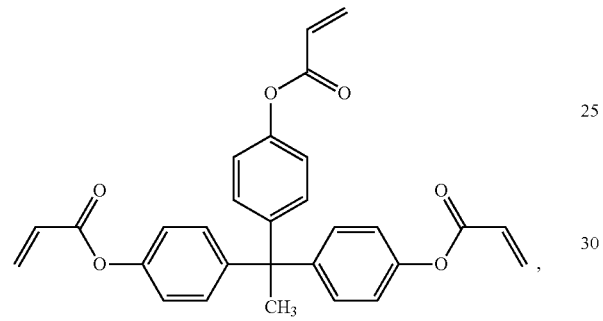
(I-2)
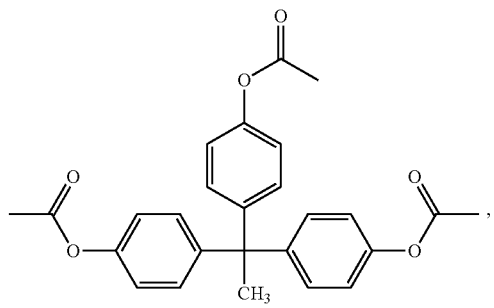
(I-9)
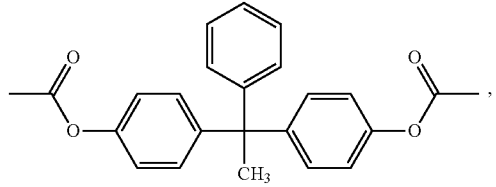
(I-10)
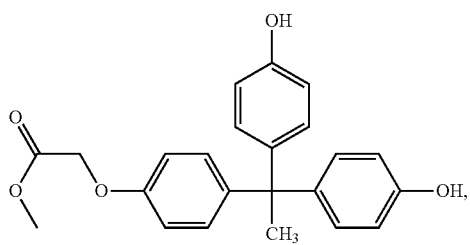
(I-11)
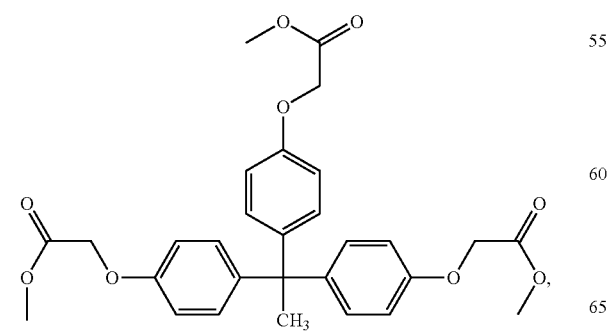
(I-3), (I-4)
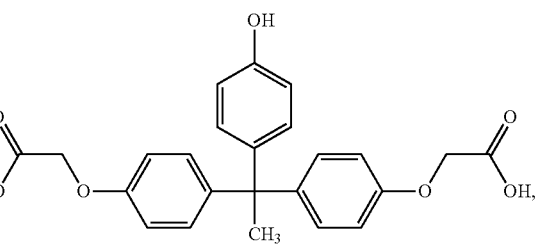
(I-12)

(I-13)
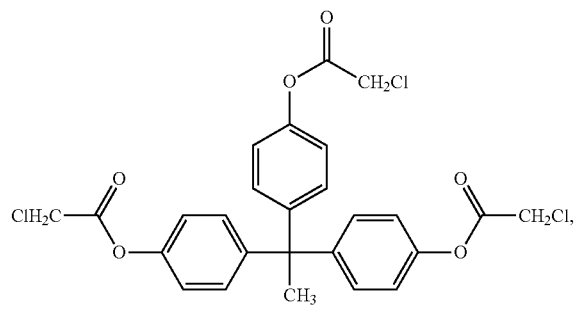
(I-3)
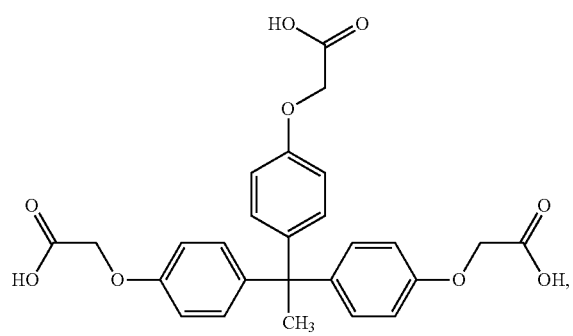
(I-14)
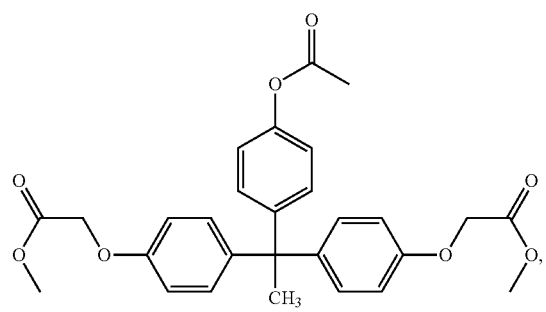
(I-4)
(I-15)
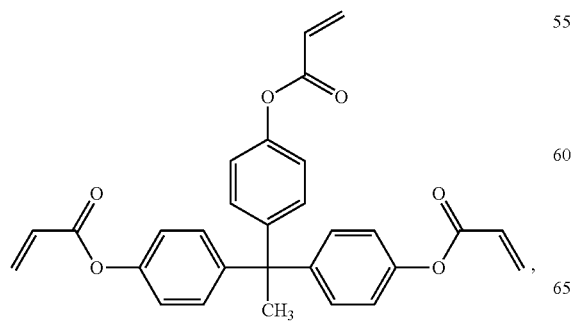
or a pharmaceutically acceptable salt thereof.
2. A method of treating rheumatoid arthritis, psoriasis, ankylosing spondylitis, Crohn's disease, or ulcerative colitis comprising administering to a patient in need of such treatment an effective amount of a pharmaceutical composition comprising an excipient and a compound having a structure:
(I-2)
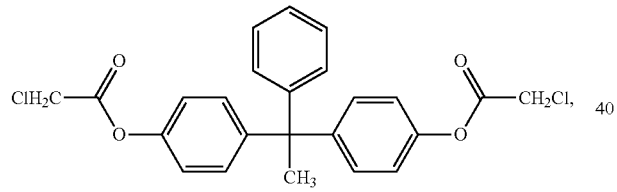
(I-9)
(I-10)
(I-11)
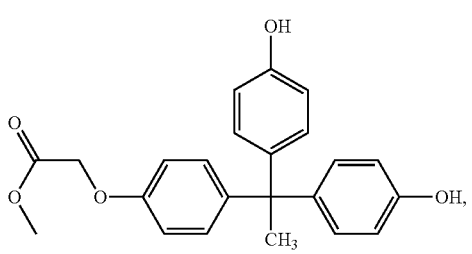

(I-12)
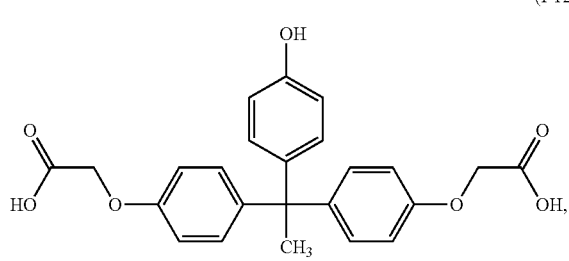
(I-14)
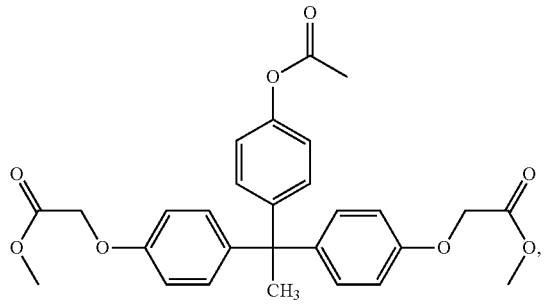
(I-13)
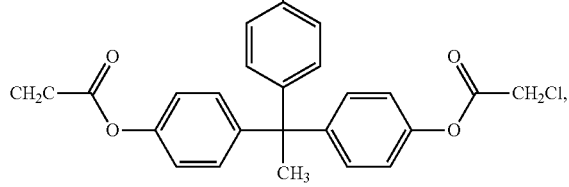
(I-15)
or a pharmaceutically acceptable salt thereof.
3. The method of claim 2, wherein the pharmaceutical composition is in the form of a capsule or tablet.
4. The method of claim 3, wherein the capsule or tablet contains the compound having a structure of formula (I) in an amount in the range of about 25 mg to about 200 mg.
* * * * *